US006413935B1

(12) United States Patent
Sette et al.

(10) Patent No.: US 6,413,935 B1
(45) Date of Patent: *Jul. 2, 2002

(54) INDUCTION OF IMMUNE RESPONSE AGAINST DESIRED DETERMINANTS

(75) Inventors: Alessandro Sette, La Jolla; Federico Gaeta, San Rafael; Howard M. Grey, La Jolla; John Sidney; Jeffrey L. Alexander, both of San Diego, all of CA (US)

(73) Assignee: Epimmune Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/788,822

(22) Filed: Jan. 23, 1997

Related U.S. Application Data

(63) Continuation-in-part of application No. 08/305,871, filed on Sep. 14, 1994, now Pat. No. 5,736,142, which is a continuation-in-part of application No. 08/121,101, filed on Sep. 14, 1993, now abandoned.
(60) Provisional application No. 60/010,510, filed on Jan. 24, 1996.

(51) Int. Cl.$^7$ .............................................. A61K 38/00

(52) U.S. Cl. ...................... 514/14; 530/402; 530/403; 530/300; 530/327; 424/185.1; 424/193.1

(58) Field of Search .................... 530/402, 403, 530/300, 324; 424/185.1, 193.1; 514/14

(56) References Cited

U.S. PATENT DOCUMENTS

| | | | | |
|---|---|---|---|---|
| 4,557,931 A | * | 12/1985 | Irie et al. ....................... | 424/88 |
| 5,114,713 A | * | 5/1992 | Sinigaglia et al. ........ | 424/185.1 |
| 5,196,512 A | | 3/1993 | Bianchi et al. | |
| 5,549,883 A | * | 8/1996 | Srinivasan et al. ......... | 424/1.45 |
| 5,736,142 A | * | 4/1998 | Sette et al. ............... | 424/185.1 |

FOREIGN PATENT DOCUMENTS

| | | |
|---|---|---|
| EP | 0 534 615 A2 | 3/1993 |
| WO | WO 92/02543 A1 | 2/1992 |
| WO | WO 93/05011 A1 | 3/1993 |
| WO | WO 9420127 A | 9/1994 |
| WO | WO 9507707 A | 3/1995 |

OTHER PUBLICATIONS

Reminton's Pharmaceutical Sciences, 18th edition, p. 1398, 1990.*
Borras–Cuesta et al., "Engineering of Immunogenic Peptides by Co–Linear Synthesis of Determinants Recognized by B and T Cells," *Eur. J. Immunol.* vol. 17:1213–1215 (1987).
Brett et al., "Fine Specificity of T Cell Recognition of the Same Peptide in Association With Different I–A Molecules," *Journal of Immunology*, vol. 143 No. 3 771–779 (Aug. 1989).

Clarke et al., "Improved Immunogenicity of a Peptide Epitope After Fusion to Hepatitis B Core Protein," *Nature*, vol. 330, 381–384 (Nov. 1987)
DiGeorge et al., "Immune Responses of Seven Different 'Promiscuous' T–Cell Epitopes on Chimeric Peptide (1997) Vaccine Design," *Peptide Vaccines and Immunology*, pp 732–733, The Ohio State University, Columbus, OH 43210.
Fern et al., "Promiscuous Malaria Peptide Epitope Stimulates CD45Ra T Cells From Peripheral Blood of Nonexposed Donors," *Journal of Immunology*, vol. 148:907–913 (1992).
Ferrari et al., "Identification of Immunodominant T Cell Epitopes of the Hepatitis B Virus Nucleocapsid Antigen," *J. Clin. Invest.* vol. 88:214–222 pp. 168–170 (Jul. 1991).
Francis et al., "Non–Responsiveness to a Foot–and–Mouth Disease Virus Peptide Overcome by Addition of Foreign Helper T–Cell Determinants," *Nature*, vol. 330 (Nov. 1987).
Greenstein et al., "A Universal T Cell Epitope–Containing Peptide From Hepatitis B Surface Antigen Can Enhance Antibody Specific for HIV gp120," *Journal of Immunology* vol. 148:3970–3977 No. 12 (Jun. 1992).
Ho et al., "Identification of Two Promiscuous T Cell Epitopes from Tetanus Toxin*," *Eur. J. Immunol.* vol. 20:477–483 (1990).
Kaumaya et al., "Immunogenicity and Antigenicity of a Promiscuous T–Cell Epitope and Topographic B–Cell Determinant of the Protein Antigen LDH–$C_4$," *Peptides Chemistry and Biology*, Proceedings of the Twelth American Peptide Symposium Jun. 16–21, 1991, Cambridge, Massachusetts, pp883–885.
Kaumaya et al., "A Universal HTLV–I Template Vaccine Incorporating Cytotoxic, Neutralizing and Promiscuous Epitope," *Peptides, Vaccines and Immunology*, pp 712–714 The Ohio State University, Columbus, OH 43210.
Meister et al., "Two Novel T Cell Epitope Prediction Algorithms Based on MHC–Binding Motifs; Comparison of Predicted and Published Epitopes from *Mycobacterium tuberculosis* and HIV Protein Sequences," *Vaccine* vol. 13(6):581–591 (1995).
Milich et al., "Antibody Production to the Nucleocapsid and Envelope of the Hepatitis B Virus Primed by a Single Synthetic T Cell Site" *Nature* vol. 329 pp. 547–549(Oct. 1987).
O'Sullivan et al., "Characterization of the Specificity of Peptide Binding To Four Dr Haplotypes," *Journal of Immunology* vol. 145:1799–1808 (Sep. 1990).

(List continued on next page.)

Primary Examiner—Patrick J. Nolan
(74) Attorney, Agent, or Firm—Townsend and Townsend and Crew LLP

(57) ABSTRACT

The present invention provides compositions and methods of inducing immune response in patients. In particular, it provides compositions useful in inducing humoral resposes against desired immunogens, particularly polysaccharides.

52 Claims, 6 Drawing Sheets-

OTHER PUBLICATIONS

O'Sullivan et al., "Truncation Analysis of Several Dr Binding Epitopes," *Journal of Immunology* vol. 146:1240–1246 (Feb. 1991).

O'Sullivan et al., "On the Interaction of Promiscuous Antigenic Peptides with Different Dr Alleles," *Journal of Immunology* vol. 147:2663–2669 (Oct. 1991).

Panina–Bordignon et al., "Universally Immunogenic T Cell Epitopes: Promiscuous Binding to Human MHC Class II and Promiscuous Recognition by T Cells," *Eur. J Immunol.* vol. 19:2237–2242 (1989).

Partidos et al., "Prediction and Indentification of a T Cell Epitope in the Fusion Protein of Measles Virus Immunodominant in Mice and Humans," *Journal of General Virology* vol. 71:2099–2105 (1990).

Powell, et al., "Peptide Stability in Drug Development. II. Effect of Single Amino Acid Substitution and Glycosylation on Peptide Reactivity in Human Serum," *Pharmaceutical Research* vol. 10(9) (1993).

Sinigaglia et al., "A Malaria T–Cell Epitope Recognized in Association with Most Mouse and Human MHC Class II Molecules," *Nature* vol. 336:22/29 (Dec. 1988).

Stagg et al., "Primary Human T–Cell Responses to the Major Outer Membrane Protein of *Chlamydia trachomatis*," *Immunology* vol. 79:1–9 (1993).

Wang et al., "Directionality in 'promiscuous' T–Cell Epitope Selection on Colinear B– and T–Cell Constructs," *Peptide Vaccines and Immunology*, pp. 753–754, The Ohio State University, Columbus, OH 43210.

Alexander, et al., *Immunity* 1(9):751 (1994).

Ishioka, et al., *J. Immunol.* 148(8):2446 (1992).

Ishioka, et al., *Springer Seminars in Immunopathology* 15(2/3):293 (1993).

Hervás–Stubbs, et al., *Vaccine* 12(10):867 (1994).

Bartolini, et al., *Vaccine* 13(5):463 (1995).

Chu, et al., *Information and Immunity* 40(1):245 (1983).

* cited by examiner

```
                              SEQUENCE LISTING (1) GENERAL INFORMATION:

(iii) NUMBER OF SEQUENCES: 30

(2) INFORMATION FOR SEQ ID NO:1:

(i) SEQUENCE CHARACTERISTICS:
          (A) LENGTH: 4 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:1:

Trp Thr Leu Lys
1

(2) INFORMATION FOR SEQ ID NO:2:

(i) SEQUENCE CHARACTERISTICS:
          (A) LENGTH: 13 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:2:

Pro Lys Tyr Val Lys Gln Asn Thr Leu Lys Leu Ala Thr
1               5                   10

(2) INFORMATION FOR SEQ ID NO:3:

(i) SEQUENCE CHARACTERISTICS:
          (A) LENGTH: 24 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:3:

Gly Arg Thr Gln Asp Glu Asn Pro Val Trp His Phe Phe Lys Asn Ile
1               5                   10                  15

Val Thr Pro Arg Thr Pro Pro Pro
            20

(2) INFORMATION FOR SEQ ID NO:4:

(i) SEQUENCE CHARACTERISTICS:
          (A) LENGTH: 12 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:4:
```

```
Tyr Lys Thr Ile Ala Phe Asp Glu Glu Ala Arg Arg
1               5                   10
```

(2) INFORMATION FOR SEQ ID NO:5:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:5:

```
Tyr Ala Arg Phe Gln Ser Gln Thr Thr Leu Lys Gln Lys Thr
1               5                   10
```

(2) INFORMATION FOR SEQ ID NO:6:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:6:

```
Gln Tyr Ile Lys Ala Asn Ser Lys Phe Ile Gly Ile Thr Glu
1               5                   10
```

(2) INFORMATION FOR SEQ ID NO:7:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:7:

```
Asn Gly Gln Ile Gly Asn Asp Pro Asn Arg Asp Ile Leu
1               5                   10
```

(2) INFORMATION FOR SEQ ID NO:8:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:8:

```
Tyr Ala His Ala Ala His Ala Ala His Ala Ala His Ala Ala His Ala
1               5                   10                  15
Ala
```

(2) INFORMATION FOR SEQ ID NO:9:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:9:

Ile Ser Gln Ala Val His Ala Ala His Ala Glu Ile Asn Glu
1               5                   10

(2) INFORMATION FOR SEQ ID NO:10:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:10:

Tyr Leu Glu Asp Ala Arg Arg Leu Lys Ala Ile Tyr Glu Lys Lys Lys
1               5                   10                  15

(2) INFORMATION FOR SEQ ID NO:11:

(i) SEQUENCE CHARACTERISTICS:
        (A) LENGTH: 17 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:11:

Tyr Asn Thr Asp Gly Ser Thr Asp Tyr Gly Ile Leu Gln Ile Asn Ser
1               5                   10                  15
Arg (2) INFORMATION FOR SEQ ID NO:12:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:12:

Asp Ile Glu Lys Lys Ile Ala Lys Met Glu Lys Ala Ser Ser Val Phe
1               5                   10                  15
Asn Val Val Asn Ser
            20

(2) INFORMATION FOR SEQ ID NO:13:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:13:

Tyr Ser Gly Pro Leu Lys Ala Glu Ile Ala Gln Arg Leu Glu Asp Val
1               5                   10                  15

(2) INFORMATION FOR SEQ ID NO:14:

```
    (i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:14:

Pro His His Thr Ala Leu Arg Gln Ala Ile Leu Cys Trp Gly Glu Leu
1               5                   10                  15

Met Thr Leu Ala
            20

(2) INFORMATION FOR SEQ ID NO:15:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:15:

Ala Ala Ala Ala Ala Ala Ala Ala Ala Ala Ala Ala Ala
1               5                   10

(2) INFORMATION FOR SEQ ID NO:16:

(i) SEQUENCE CHARACTERISTICS:
        (A) LENGTH: 13 amino acids
        (B) TYPE: amino acid
        (C) STRANDEDNESS:

(D) TOPOLOGY: linear (ii) MOLECULE TYPE: peptide (xi) SEQUENCE DESCRIPTION: SEQ ID NO:16:

Thr Pro Pro Ala Tyr Arg Pro Pro Asn Ala Pro Ile Leu
1               5                   10

(2) INFORMATION FOR SEQ ID NO:17:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:17:

His Ser Leu Gly Lys Trp Leu Gly His Pro Asp Lys Phe
1               5                   10

(2) INFORMATION FOR SEQ ID NO:18:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:18:

Asn Thr Asp Gly Ser Thr Asp Tyr Gly Ile Leu Gln Ile Asn Ser Arg
```

```
1               5                  10                 15
```

(2) INFORMATION FOR SEQ ID NO:19:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:19:

```
Gly Asp Arg Ala Asp Gly Gln Pro Ala Gly Asp Arg Ala Asp Gly Gln
1               5                  10                  15
Pro Ala
```

(2) INFORMATION FOR SEQ ID NO:20:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:20:

```
Gly Asp Arg Ala Asp Gly Gln Pro Ala Gly Asp Arg Ala Asp Gly Gln
1               5                  10                  15
Pro Ala Gly Asp Arg Ala Asp Gly Gln Pro Ala
                20                  25
```

(2) INFORMATION FOR SEQ ID NO:21:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "OTHER"
            /note= "Xaa = cyclohexylalanine"

(ix) FEATURE:
        (A) NAME/KEY: Modified-site
        (B) LOCATION: 12
        (D) OTHER INFORMATION: /product= "OTHER"
            /note= "Xaa = alaninamide"

(xi) SEQUENCE DESCRIPTION: SEQ ID NO:21:

```
Ala Lys Xaa Val Ala Ala Trp Thr Leu Lys Ala Xaa
1               5                  10
```

(2) INFORMATION FOR SEQ ID NO:22:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (ix) FEATURE:

(A) NAME/KEY: Modified-site
        (B) LOCATION: 3
        (D) OTHER INFORMATION: /product= "OTHER"
            /note= "Xaa = cyclohexylalanine"

(xi) SEQUENCE DESCRIPTION: SEQ ID NO:22:

Ala Ala Xaa Ala Ala Ala Lys Thr Ala Ala Ala Ala Ala
1               5                   10

(2) INFORMATION FOR SEQ ID NO:23:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "OTHER"
            /note= "Xaa = cyclohexylalanine"

(xi) SEQUENCE DESCRIPTION: SEQ ID NO:23:

Ala Ala Xaa Ala Ala Ala Ala Thr Leu Lys Ala Ala Ala
1               5                   10

(2) INFORMATION FOR SEQ ID NO:24:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "OTHER"
            /note= "Xaa = cyclohexylalanine"

(xi) SEQUENCE DESCRIPTION: SEQ ID NO:24:

Ala Ala Xaa Val Ala Ala Ala Thr Leu Lys Ala Ala Ala
1               5                   10

(2) INFORMATION FOR SEQ ID NO:25:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "OTHER"
            /note= "Xaa = cyclohexylalanine"

(xi) SEQUENCE DESCRIPTION: SEQ ID NO:25:

Ala Ala Xaa Ile Ala Ala Ala Thr Leu Lys Ala Ala Ala
1               5                   10

(2) INFORMATION FOR SEQ ID NO:26:

```
    (i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "OTHER"
            /note= "Xaa = cyclohexylalanine"

(xi) SEQUENCE DESCRIPTION: SEQ ID NO:26:

Ala Lys Xaa Val Ala Ala Trp Thr Leu Lys Ala Ala Ala
1               5                   10

(2) INFORMATION FOR SEQ ID NO:27:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:27:

Ala Lys Phe Val Ala Ala Trp Thr Leu Lys Ala Ala Ala
1               5                   10

(2) INFORMATION FOR SEQ ID NO:28:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "OTHER"
            /note= "Xaa = cyclohexylalanine, Tyr,
            Phe or conservative substitutions
            therefor"

(ix) FEATURE:
        (A) NAME/KEY: Modified-site
        (B) LOCATION: 7..8
        (D) OTHER INFORMATION: /product= "OTHER"
            /note= "Xaa may be present or absent"

(xi) SEQUENCE DESCRIPTION: SEQ ID NO:28:

Xaa Xaa Xaa Xaa Xaa Xaa Xaa Xaa Thr Leu Lys Xaa Xaa
1               5                   10

(2) INFORMATION FOR SEQ ID NO:29:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
```

```
        (D) OTHER INFORMATION: /product= "OTHER"
            /note= "Xaa = cyclohexylalanine, Tyr,
            Phe or conservative substitutions
            therefor"

(ix) FEATURE:
        (A) NAME/KEY: Modified-site
        (B) LOCATION: 7..8
        (D) OTHER INFORMATION: /product= "OTHER"
            /note= "Xaa may be present or absent"

(xi) SEQUENCE DESCRIPTION: SEQ ID NO:29:

Xaa Xaa Xaa Xaa Xaa Xaa Xaa Xaa Lys Thr Xaa Xaa
1               5                   10

(2) INFORMATION FOR SEQ ID NO:30:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "OTHER"
            /note= "Xaa = cyclohexylalanine, Tyr,
            Phe or conservative substitutions
            therefor"

(ix) FEATURE:
        (A) NAME/KEY: Modified-site
        (B) LOCATION: 7..8
        (D) OTHER INFORMATION: /product= "OTHER"
            /note= "Xaa may be present or absent"

(xi) SEQUENCE DESCRIPTION: SEQ ID NO:30:

Xaa Xaa Xaa Xaa Xaa Xaa Xaa Xaa Trp Thr Leu Lys Xaa Xaa
1               5                   10
```

INDUCTION OF IMMUNE RESPONSE AGAINST DESIRED DETERMINANTS

REFERENCE TO RELATED APPLICATIONS

This application is a continuation-in-part of provisional patent application No. 60/010,510, filed Jan. 24, 1996 and a continuation-in-part to U.S. patent application Ser. No. 08/305,871, filed Sep. 14, 1994, now U.S. Pat. No. 5,736, 142, issued Apr. 7, 1998, which is a continuation-in-part of U.S. Ser. No. 08/121,101 filed Sep. 14, 1993, now abandoned, all of which are incorporated herein by reference.

BACKGROUND OF THE INVENTION

It is generally known in the art that the nature of the immune response raised against a particular vaccine antigen is important to the overall effectiveness of the vaccine. In the case of carbohydrate antigens, a large variety of approaches has been explored in attempts to enhance their immunogenicity, including chemical modification (Jennings, et al. in *Towards Better Carbohydrate Vaccines* Bell and Torrigiani (eds) pp 11–17, J. Wiley & Sons, London, 1987), administration with adjuvants, noncovalent complexing with proteins, covalent attachment to immunogenic protein carriers (Schneerson, et al. in *Towards Better Carbohydrate Vaccines*, supra pp 307–327), and replacement of the carbohydrate epitope by a protein replica, either peptides synthesized de novo (so-called mimitopes, Geyson, et al. in *Towards Better Carbohydrate Vaccines*, supra, pp 103–118) or antiidiotypic antibodies (Soederstroem in *Towards Better Carbohydrate Vaccines*, supra, pp 119–138).

Covalent attachment of carbohydrate antigens to immunogenic T-dependent protein carriers is known (see, e.g, Schneerson, et al., 152:361–376 (1980); Lepow, et al., *J. Pediatr.* 106:185–189 (1985); Chu, et al., *Infect. Immun.*, 50:245–256 (1983); Marborg et al., Am. Chem. Soc.) 108:5282–5287 (1985); Anderson et al., *Infect. Immun.*, 39:233–238 (1983); Bartoloni, et al., *Vaccine* 13:463–470 (1995); and Wessels, et al., *J. Infect. Dis.* 171:879–884 (1995)).

Immunogenic peptides, containing epitopes recognized by T helper cells, have been found to be useful in inducing immune responses. The use of helper peptides to enhance antibody responses against particular determinants is described for instance in Hervas-Stubbs, et al., *Vaccine* 12:867–871 (1994).

Although allele-specific polymorphic residues that line the peptide binding pockets of MHC alleles tend to endow each allele with the capacity to bind a unique set of peptides, there are many instances in which a given peptide has been shown to bind to more than one MHC allele. This has been best documented in the case of the human DR isotype, in which it has been noted that several DR alleles appear to recognize similar motifs, and independently, several investigators reported degenerate binding and/or recognition of certain epitopes in the context of multiple DR types, leading to the concept that certain peptides might represent "universal" epitopes (Busch, et al., *Int. Immunol.* 2:443–451 (1990); Panina-Bordignon, et al., *Eur. J. Immunol.* 19:2237–2242 (1989); Sinigaglia, et al., *Nature* 336:778–780 (1988); O'Sullivan, et al., *J. Immunol.* 147:2663–2669 (1991); Roache, et al., *J. Immunol.* 144:1849–1856 (1991); Hill, et al., *J. Immunol.* 147:189–197 (1991)). Although, the previously reported peptides do have the capacity to bind to several DR alleles, they are by no means universal.

Pan-DR binding (PADRE) peptides have been described in WO 95/07707 and Alexander, et al., *Immunity* 1:751–761 (1994).

For example, preferred pan DR peptides have the formula $R_1$-$R_2$-$R_3$-$R_4$-$R_5$, where $R_1$ is a D-amino acid followed by alanine or lysine, $R_2$ is cyclohexylalanine, tyrosine, or phenylalanine, $R_3$ is 3 or 4 amino acids each of which is selected from the group consisting of alanine, isoleucine, serine and valine; $R_4$ is threonine-leucine-lysine, lysine-threonine, or tryptophan-threonine-leucine-lysine; and $R_5$ consists of 2 to 4 amino acids followed by a D-amino acid, where each 2 to 4 amino acids is independently selected from the group consisting of alanine, serine, and valine.

The sentence above is not new matter because the sentence (from page 4, lines 17–28 of U.S. Ser. No. 08/305,871) is incorporated by reference in the present application. The present application is a continuation-in-part of U.S. Ser. No. 08/305,871, filed Sep. 14, 1994, now U.S. Pat. No. 5,736, 142, issued Apr. 7, 1998. U.S. Ser. No. 08/305,871 is incorporated by reference in the present application on page 1, lines 12–14. Therefore, the language was always a part of the specification and is not new matter. These peptides have been shown to help in the generation of a CTL response against desired protein antigens.

However, the prior art fails to teach compounds or compositions that provide an effective humoral response. For example, in the case of carbohydrate immunogens, antibody responses have traditionally been predominantly of short-term expression of IgM followed by an inconsistent IgG response. Such a response is generally not as effective in producing long term protection against the immunogen as an IgG-mediated response. The present invention addresses these and other needs.

BRIEF SUMMARY OF THE INVENTION

The present invention provides compositions comprising a PADRE oligopeptide of less than about 50 amino acid residues and an antigenic determinant, wherein the oligopeptide and antigenic determinant are optionally covalently attached to each other. The antigenic determinant can be from a bacterium, a virus, a cancer cell, a fungus, or a parasite. When the PADRE oligopeptide and the antigenic determinant are covalently attached to each other, they will be either directly linked or attached by means of a linking group which preferably comprises a cysteine residue.

In one group of embodiments, the PADRE peptide is selected from the group consisting of aAXAAAKTAAAAa, aAXAAAATLKAAa, aAXVAAATLKAAa, aAXIAAATLKAAa, aKXVAAWTLKAAa, and aKFVAAWTLKAAa wherein a is D-alanine, A is L-alanine, X is cyclohexylalanine, K is lysine, T is threonine, L is leucine, V is valine, I is isoleucine, W is tryptophan, and F is phenylalanine. More preferably, the PADRE peptide is aKXVAAWTLKAAa. In other groups of embodiments, the termini of the peptides can be either in the D- or L-form.

Additionally, the present invention provides a composition for eliciting an immune response to an immunogenic carbohydrate, the composition comprising a PADRE oligopeptide of less than about 50 residues and at least one carbohydrate epitope. Preferably, the PADRE peptide has the formula $R_1$-$R_2$-$R_3$-$R_4$-$R_5$, (SEQ ID NOS:28–30 No: 2) proceeding from the N-terminus to the C-terminus, wherein $R_1$ consists of at least 2 residues; $R_2$ is selected from the group consisting of a cyclohexylalanine residue, a tyrosine residue, a phenylalanine residue and conservative substitutions therefor; $R_3$ is 3 to 5 amino acid residues; $R_4$ is selected from the group consisting of threonine-leucine-lysine, lysine-threonine, and tryptophan-threonine-leucine-lysine, and conservative (SEQ ID NO:1) substitutions therefor; and $R_5$ consists of at least 2 residues.

BRIEF DESCRIPTION OF THE FIGURES

FIG. 2A shows results of a second stimulation, and FIG. 2B shows results of a third stimulation. The maximum Δ cpm obtained is plotted on the ordinate.

FIG. 3A shows results of a second stimulation, and FIG. 3B shows results of a third stimulation. The maximum Δ cpm obtained is plotted on the ordinate.

DETAILED DESCRIPTION OF THE INVENTION

A. Definitions

Figure 1A:
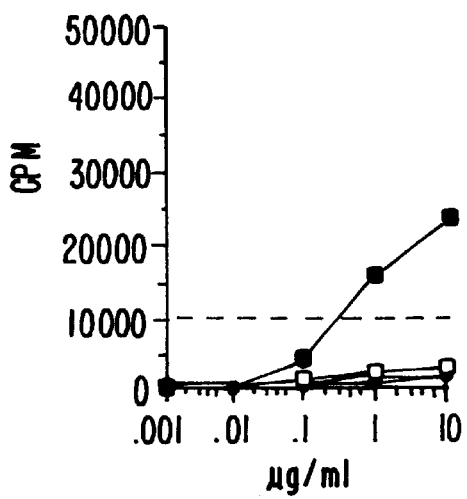
FIGS. 1A–1F show representative responses for three of twelve different donors. Antigen specific T cell responses from human PBMC T cell lines generated on day 0 by addition of either peptide 965.10 (closed square), 906.09 (open square), 760.50 (closed circle), or Tetanus toxoid 830–843 (open circle) as assayed on day 14 (second stimulation, FIGS. 1A, 1B, 1C) and day 28 (third stimulation, FIGS. 1D, 1E, 1F). A representative of two independent experiments is shown.
Figure 1B:
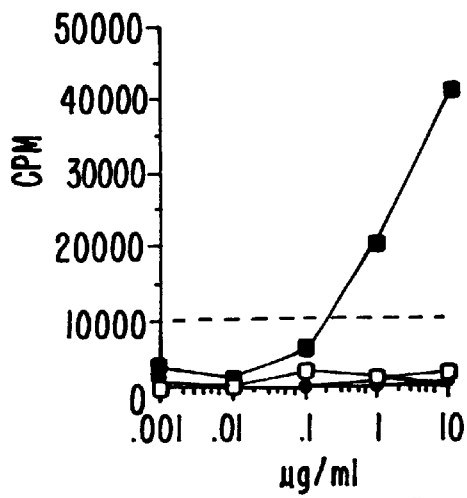
Figure 1C:
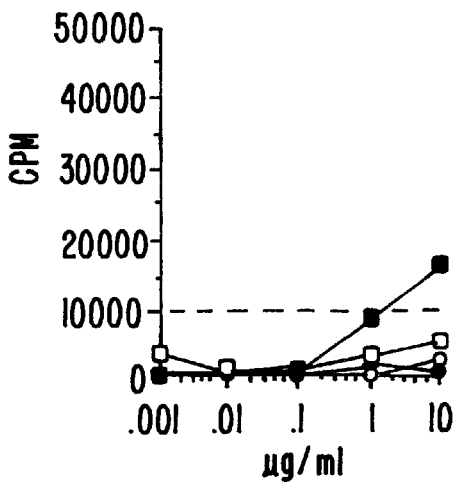
Figure 1D:
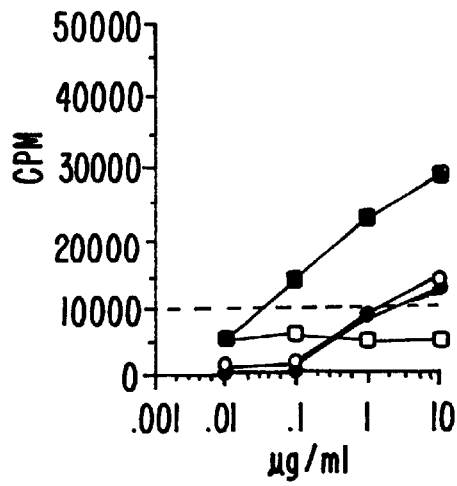
Figure 1E:
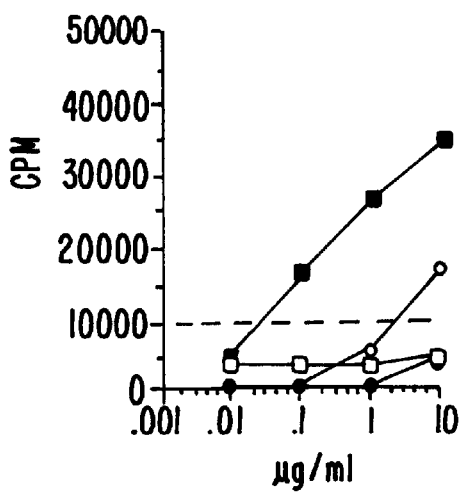
Figure 1F:
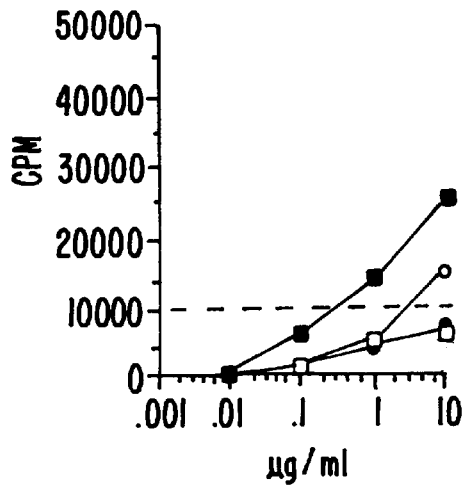

An oligopeptide or peptide as used herein refers to a chain of at least four amino acid or amino acid mimetics, preferably at least six, more preferably eight to ten, sometimes eleven to fourteen residues, and usually fewer than about fifty residues, more usually fewer than about twenty-five, and preferably fewer than fifteen, e.g., eight to fourteen residues. The oligopeptides or peptides can be a variety of lengths, either in their neutral (uncharged) forms or in forms which are salts, and either free of modifications such as glycosylation, side chain oxidation, or phosphorylation or containing these modifications, subject to the condition that the modification not destroy the biological activity of the polypeptides as herein described.

When referring to an amino acid residue in a peptide, oligopeptide or protein the terms "amino acid residue", "amino acid" and "residue" are used interchangeably and, as used herein, mean an amino acid or amino acid mimetic joined covalently to at least one other amino acid or amino acid mimetic through an amide bond or amide bond mimetic.

As used herein, the term "amino acid", when unqualified, refers to an "L-amino acid" or L-amino acid mimetic.

Although the peptides will preferably be substantially free of other naturally occurring proteins and fragments thereof, in some embodiments the peptides can be synthetically conjugated to native fragments or particles.

As used herein, the term "biological activity" means the ability to bind an appropriate MHC molecule and, in the case of peptides useful for stimulating immune responses, induce a T helper response, which in turn helps to induce an immune response against a target immunogen or immunogen mimetic. In the case of peptides useful for stimulating antibody responses, the peptide will induce a T helper response, which in turn helps induce a humoral response against the target immunogen.

A "pan DR-binding peptide (PADRE)" of the invention is a peptide capable of binding at least about 7 of the 12 most common DR alleles (DR1, 2w2b, 2w2a, 3, 4w4, 4w14, 5, 7, 52a, 52b, 52c, and 53).

Throughout this disclosure, results are expressed in terms of IC50s. Given the conditions in which the assays are run (i.e., limiting MHC and labeled peptide concentrations), these values approximate $K_D$ values. It should be noted that IC50 values can change, often dramatically, if the assay conditions are varied, and depending on the particular reagents used (e.g., MHC preparation, etc.). For example, excessive concentrations of MHC will increase the apparent measured IC50 of a given ligand.

An alternative way of expressing the binding data, to avoid these uncertainties, is as a relative value to a reference peptide. The reference peptide is included in every assay. As a particular assay becomes more or less sensitive, the IC50 of the peptides tested may change somewhat. However, the binding relative to the reference peptide will not change. For example, in an assay run under conditions such that the IC50 of the reference peptide increases 10-fold, all IC50 values will also shift approximately 10-fold. Therefore, to avoid ambiguities, the assessment of whether a peptide is a good, intermediate, weak, or negative binder should be based on its IC50, relative to the IC50 of the standard peptide.

If the IC50 of the standard peptide measured in a particular assay is different from that reported in Table 1, then it should be understood that the threshold values used to determine good, intermediate, weak, and negative binders should be modified by a corresponding factor.

The PADRE peptides of the invention, in addition to promoting an immune response against a second determinant, can also serve as target immunogens, themselves. Thus, for instance, in the case in which the PADRE peptide is linked to a carbohydrate epitope, the immune response may be to both the PADRE peptide and the carbohydrate epitope.

The terms "immunogen" and "antigen" are used interchangeably and mean any compound to which a cellular or humoral immune response is to be directed against.

As used herein, the term "antigenic determinant" is any structure that can elicit, facilitate, or be induced to produce an immune response, for example carbohydrate epitopes, lipids, proteins, peptides, or combinations thereof A "CTL epitope" of the present invention is one derived from selected epitopic regions of potential target antigens, such as tumor associated antigens, including, but not limited to, renal cell carcinoma, breast cancer, carcinoembryonic antigens, melanoma (MAGE-1) antigens, and prostate cancer specific antigen, hepatitis C antigens, Epstein-Barr virus antigens, HIV-1 and HIV-2 antigens, and papilloma virus antigens.

TABLE I

| Allele | Assay standard | Sequence | Avg. IC50 nM | SEQ ID NO: |
|---|---|---|---|---|
| DR1 | HA 307–319 | PKYVKQNTLKLAT | 5 | 2 |
| DR2w2b | MBP 78–101 | GRTQDENPVWHFFKNIVTPRTPPP | 9.1 | 3 |
| DR3 | MT 65 kd 3–13 | YKTIAFDEEARR | 250 | 4 |
| DR4w4 | HA 307–319 | PKYVKQNTLKLAT | 45 | 2 |
| DR4w14 | 717.01 combinatorial | YARFQSQTTLKQKT | 50 | 5 |
| DR5 | Tet Tox 830–843 | QYIKANSKFIGITE | 20 | 6 |
| DR7 | Tet Tox 830–843 | QYIKANSKFIGITE | 25 | 6 |
| DR52a | Tet tox 1272–1284 | NGQIGNDPNRDIL | 470 | 7 |
| DRw53 | 717.01 combinatorial | YARFQSOTTLKQKT | 58 | 5 |
| Dr2w2a | Tet Tox 830–843 | QYIKANSKFIGITE | 20 | 6 |
| DQ3.1 | ROIV | YAHAAHAAHAAHAAHAA | 15 | 8 |
| IAb | ROIV | YAHAAHAAHAAHAAHAA | 28 | 8 |
| IAd | Ova 323–326 | ISQAVHAAHAEINE | 110 | 9 |
| IEd | Iambda rep 12–26 | YLEDARRLKAIYEKKK | 170 | 10 |
| IAs | ROIV | YAHAAHAAHAAHAAHAA | 54 | 8 |
| IAk | HEL 46–61 | YNTDGSTDYGILOINSR | 20 | 11 |
| IEk | Iambda rep 12–26 | YLEDARRLKAIYEKKK | 28 | 10 |

A "humoral response" of the present invention is an antibody-mediated immune response directed towards various regions of an antigenic determinant. One of skill will recognize that a humoral response may also be induced against a PADRE peptide, wherein the PADRE peptide would also be included with the determinant. Thus the elicited immune response may be against both the antibody inducing determinant and the PADRE peptide.

A "carbohydrate epitope" as used herein refers to a carbohydrate structure, present as a glycoconjugate, e.g., glycoprotein, glycopeptide, glycolipid, and the like, DNA, RNA, or a polysaccharide, oligosaccharide, or monosaccharide against which an immune response is desired. The carbohydrate epitope may induce a wide range of immune responses. One of skill will recognize that various carbohydrate structures exemplified herein can be variously modified according to standard methods, without adversely affecting antigenicity. For instance, the monosaccharide units of the saccharide may be variously substituted or even replaced with small organic molecules, which serve as mimetics for the monosaccharide.

The phrases "isolated" or biologically pure" refer to material which is substantially or essentially free from components which normally accompany it as found in its native state. Thus, the peptides of the present invention do not contain materials normally associated with their in situ environment, e.g., MHC Class I molecules with antigen presenting cells. Even if a protein has been isolated to a homogeneous or dominant band in an electrophoretic gel, there are trace contaminants in the range of 5–10% of native protein which co-purify with the desired protein. Isolated peptides of this invention do not contain such endogenous co-purified protein.

A "linker" as used herein is any compound used to provide covalent linkage, and spacing between two functional groups (e.g., a PADRE peptide and a desired immunogen). Typically, the linker comprises neutral molecules, such as aliphatic carbon chains, amino acids or amino acid mimetics, which are substantially uncharged under physiological conditions and may have linear or branched side chains. In some cases, the linker may, itself, be immunogenic, although non-therapeutically directed. Various linkers useful in the invention are described in more detail, below. Additionally, the verbs "link" and "conjugate" are used interchangeably herein and refer to covalent attachment of two or more species.

The term "T cell clone" refers to a group of T cells that are progeny of a single virgin lymphocyte and express identical T cell receptor proteins. The term "virgin" lymphocyte is used here as it is used in Stites et al. *Basic and Clinical Immunology, 8th Edition,* Prentice Hall, Englewood Cliffs, N.J. (1994) which is incorporated herein by reference.

A "T helper peptide" as used herein refers to a peptide recognized by the T cell receptor of T helper cells. The PADRE peptides of the present invention are T helper peptides.

B. PADRE Peptides and Antigenic Determinants

The compositions of the invention generally comprise two components, a PADRE peptide conjugated to or admixed with one or more antigenic determinants. The embodiments in which the two components are linked will have the following general structure:

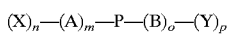

wherein, P is a PADRE peptide of the invention; X and Y can be the same or different and are antigenic determinants, e.g., carbohydrate epitopes, lipids, proteins, peptides, or combinations thereof, and A and B can be the same or different and are linkers. The letters n through p can be either 1 or 0, with the proviso that n and p cannot both be 0, for antigenic determinants. Each of the components of the compositions of the invention is described in more detail, below.

The present invention is useful for eliciting an immune response to antigenic determinants, typically, a humoral response to a carbohydrate immunogen.

The nomenclature used to describe peptide compounds follows the conventional practice wherein the amino group is presented to the left (the N-terminus) and the carboxyl group to the right (the C-terminus) of each amino acid residue. In the amino acid structure formulae, each residue is generally represented by standard three letter or single letter designations. The L-form of an amino acid residue is represented by a capital single letter or a capital first letter of a three-letter symbol, and the D-form for those amino acids having D-forms is represented by a lower case single letter or a lower case three letter symbol. Glycine has no asymmetric carbon atom and is simply referred to as "Gly" or G.

The nomenclature used to describe carbohydrates includes the following abbreviations: Ara=arabinosyl; Fru=fructosyl; Fuc=fucosyl; Gal=galactosyl; GalNAc=N-acetylgalacto; Glc=glucosyl; GlcNAc=N-acetylgluco; Man=mannosyl; and NeuAc=sialyl (N-acetylneuraminyl).

Carbohydrates are considered to have a reducing end and a non-reducing end, whether or not the saccharide at the reducing end is in fact a reducing sugar. In accordance with accepted nomenclature, carbohydrates are depicted herein with the nonreducing end on the left and the reducing end on the right.

All carbohydrates herein are described with the name or abbreviation for the non-reducing saccharide (e.g., Gal), followed by the configuration of the glycosidic bond ($\alpha$ or $\beta$), the ring bond, the ring position of the reducing saccharide involved in the bond, and then the name or abbreviation of the reducing saccharide (e.g., GlcNAc). The linkage between two sugars may be expressed, for example, as 2,3, 2→3, or (2,3). Each saccharide is a pyranose.

1. Pan Dr-binding Peptides

The present invention provides methods useful for identification of modifications to a starting peptide which broaden its specificity. For instance, International Application WO 92/02543 describes methods suitable for identifying peptides capable of binding DR molecules. WO 92/02543 describes the use of hemagglutinin from the influenza virus ("HA"), as the source of peptides specifically reacting with HLA-DR. Portions of the protein are screened for reactivity to provide sequences which bind the appropriate DR molecule, such as DR1, DR4w4 or DR4w14.

Once an immunogen or peptide thereof which binds to the selected MHC molecule is identified, a "core binding region" of the antigen or peptide may be determined by synthesizing overlapping peptides, and/or employing N-terminal or C-terminal deletions (truncations) or additions. In the determination of a core binding region and critical contact residues, a series of peptides with single amino acid substitutions may be employed to determine the effect of electrostatic charge, hydrophobicity, etc. on binding.

Within the core region, "critical contact sites," i.e., those residues (or their functional equivalents) which must be present in the peptide so as to retain the ability to bind an MHC molecule and inhibit the presentation to the T cell, may be identified by single amino acid substitutions, deletions, or insertions. In addition, one may also carry out a systematic scan with a specific amino acid (e.g., Ala) to probe the contributions made by the side chains of critical contact residues.

The peptides of the invention are relatively insensitive to single amino acid substitutions with neutral amino acids, except at essential contact sites, and have been found to tolerate multiple substitutions. Particularly preferred multiple substitutions are small, relatively neutral moieties such as Ala, Gly, Pro, or similar residues. The substitutions may be homo-oligomers or hetero-oligomers. The number and types of residues which are substituted or added depend on the spacing necessary between essential contact points and certain functional attributes which are sought (e.g., hydrophobicity versus hydrophilicity). Increased binding affinity for an MHC molecule may also be achieved by such substitutions, compared to the affinity of the parent peptide. In any event, such "spacer" substitutions should employ amino acid residues or other molecular fragments chosen to avoid, for example, steric and charge interference which might disrupt binding.

The effect of single amino acid substitutions may also be probed using D-amino acids. Such substitutions may be made using well known peptide synthesis procedures, as described in e.g., Merrifield, *Science* 232:341–347 (1986), Barany and Merrifield, *The Peptides*, Gross and Meienhofer, eds. (New York, Academic Press), pp. 1–284 (1979); and Stewart and Young, *Solid Phase Peptide Synthesis*, (Rockford, Ill., Pierce), 2d Ed. (1984).

The peptides employed in the subject invention need not be identical to peptides disclosed in the Example sections below, so long as the subject compounds are able to bind to the appropriate MHC molecules or provide for humoral or cytotoxic T lymphocytic activity against the target immunogen. Thus, one of skill will recognize that a number of conservative substitutions can be made without substantially affecting the activity of the peptide. Conservative substitutions in which an amino acid residue is replaced with another which is biologically and/or chemically similar, e.g., one hydrophobic residue for another, or one polar residue for another. The substitutions include combinations such as Gly, Ala; Val, Ile, Leu, Met; Asp, Glu; Asn, Gln; Ser, Thr; Lys, Arg; and Phe, Tyr.

In addition, the peptide or oligopeptide sequences can differ from the natural sequence by being modified by terminal-$NH_2$ acylation, e.g., by alkanoyl ($C_1$–$C_{20}$) or thioglycolyl acetylation, terminal-carboxy amidation, e.g., ammonia, methylamine, etc. In some instances these modifications may provide sites for linking to a support or other molecule.

Another approach may be used in which anchor residues that contain side chains critical for the binding to the MHC are inserted into a poly-alanine peptide of 13 residues. This approach has been used by Jardetzky, et al., *Nature* 353:326–329 (1990). They demonstrated that a polyalanine peptide which was modified with a single dominant MHC contact residue (Tyr) endowed the peptide with high affinity binding capacity for DR1. Instead of using tyrosine as the main MHC contact residue, cyclohexylalanine or phenylalanine can also be utilized, These residues are interchangeable with Tyr with respect to a peptide's capacity to bind those DR alleles capable of high affinity binding of the HA peptide, and furthermore also allow binding to MHC molecules that contain a G→V substitution at residue 86 in the DR β chain. This change affects the binding specificity of the B binding pocket in class II MHC such that tyrosine is no longer capable of effective binding, whereas cyclohexylalanine, as well as phenylalanine, can bind.

The biological activity of the peptides identified above may be assayed in a variety of systems. Typically, the ability to inhibit antigen-specific T cell activation is tested. In one exemplary protocol, an excess of peptide is incubated with an antigen-presenting cell of known MHC expression, (e.g., DR1) and a T cell clone of known antigen specificity (e.g., tetanus toxin 830–843) and MHC restriction (again, DR1), and the immunogenic peptide itself (i.e., tetanus toxin 830–843). The assay culture is incubated for a sufficient time for T cell proliferation, such as four days, and proliferation is then measured using standard procedures, such as pulsing with [$^3$H]-thymidine during the last 18 hours of incubation. The percent inhibition, compared to the controls which do not receive peptide, is then calculated.

The capacity of peptides to inhibit antigen presentation in an in vitro assay has been correlated to the capacity of the peptide to inhibit an immune response in vivo. In vivo activity may be determined in animal models, for example, by administering an immunogen known to be restricted to the particular MHC molecule recognized by the peptide, and the immunomodulatory peptide. T lymphocytes are subsequently removed from the animal and cultured with a dose range of immunogen. Inhibition of stimulation is measured by conventional means, e.g., pulsing with [$^3$H]-thymidine, and comparing to appropriate controls. Certain experimental details will of course be apparent to the skilled artisan. See also, Adorini, et al., *Nature* 334:623–625 (1988), incorporated herein by reference.

A large number of cells with defined MHC molecules, particularly MHC Class II molecules, are known and readily available from, for instance, the American Type Culture Collection ("Catalogue of Cell Lines and Hybridomas," 6th edition (1988)) Rockville, Md., U.S.A.

A preferred embodiment of the peptides of the present invention comprises modifications to the N- and C-terminal residues. As will be well understood by the artisan, the N- and C-termini may be modified to alter physical or chemical properties of the peptide, such as, for example, to affect binding, stability, bioavailability, ease of linking, and the like.

Modifications of peptides with various amino acid mimetics or d-amino acids, for instance at the N- or C-termini, are useful for instance, in increasing the stability of the peptide in vivo. Such peptides may be synthesized as "inverso" or "retroinverso" forms, that is, by replacing L-amino acids of a sequence with D-amino acids, or by reversing the sequence of the amino acids and replacing the L-amino acids with D-amino acids. As the D-peptides are substantially more resistant to peptidases, and therefore are more stable in serum and tissues compared to their L-peptide counterparts, the stability of D-peptides under physiological conditions may more than compensate for a difference in affinity compared to the corresponding L-peptide. Further, L-amino acid containing peptides with or without substitutions can be capped with a D-amino acid to inhibit exopeptidase destruction of the immunogenic peptide.

Stability can be assayed in a number of ways. For instance, peptidases and various biological media, such as human plasma and serum, have been used to test stability. See, e.g., Verhoef, et al., *Eur. J. Drug Metab. Pharmacokin.* 11:291–302 (1986); Walter, et al., *Proc. Soc. Exp. Biol. Med.* 148:98–103 (1975); Witter, et al., *Neuroendocrinology* 30:377–381 (1980); Verhoef, et al., *J. Endocrinology* 110:557–562 (1986); Handa, et al., *Eur. J. Pharmacol.* 70:531–540 (1981); Bizzozero, et al., *Eur. J. Biochem.* 122:251–258 (1982); Chang, *Eur. J. Biochem.* 151:217–224 (1985), all of which are incorporated herein by reference.

Stability may also be increased by introducing D-amino acid residues at the C- and N-termini of the peptide. Previous studies have indicated that the half-life of L-amino acid-containing peptides in vivo and in vitro, when incubated in serum-containing medium, can be extended considerably by rendering the peptides resistant to exopeptidase activity by introducing d-amino acids at the C- and N-termini.

The peptides or analogs of the invention can be modified by altering the order or composition of certain residues, it being readily appreciated that certain amino acid residues essential for biological activity, e.g., those at critical contact sites, may generally not be altered without an adverse effect on biological activity. The non-critical amino acids need not be limited to those naturally occurring in proteins, such as L$\alpha$-amino acids, or their D-isomers, but may include non-protein amino acids as well, such as $\beta$-$\gamma$-$\delta$-amino acids, as well as many derivatives of L-$\alpha$-amino acids. As discussed, a peptide of the present invention may generally comprise either L-amino acids or D-amino acids, but not D-amino acids within a core binding region.

The peptides of the invention can be prepared in a wide variety of ways. Because of their relatively short size, the peptides can be synthesized in solution or on a solid support in accordance with conventional techniques. Various automatic synthesizers are commercially available and can be used in accordance with known protocols. See, for example, Stewart and Young, *Solid Phase Peptide Synthesis*, 2d. Ed., Pierce Chemical Co. (1984), supra.

Alternatively, recombinant DNA technology may be employed wherein a nucleotide sequence which encodes an immunogenic peptide of interest is inserted into an expression vector, transformed or transfected into an appropriate host cell and cultivated under conditions suitable for expression. These procedures are generally known in the art, as described generally in Sambrook, et al., *Molecular Cloning, A Laboratory Manual*, Cold Spring Harbor Press, Cold Spring Harbor, N.Y. (1989). Thus, fusion proteins which comprise one or more peptide sequences of the invention can be used to present the appropriate T cell epitope.

As the coding sequence for peptides of the length contemplated herein can be synthesized by chemical techniques, for example, the phosphotriester method of Matteucci, et al., *J. Am. Chem. Soc.* 103:3185 (1981), modification can be made simply by substituting the appropriate base(s) for those encoding the native peptide sequence. Nucleic acid sequences that encode for appropriate linkers can then be added to the peptide coding sequence and ligated into expression vectors commonly available in the art, and the vectors used to transform suitable hosts to produce the desired fusion protein. A number of such vectors and suitable host systems are now available. For expression of the fusion proteins, the coding sequence will be provided with operably linked start and stop codons, promoter and terminator regions and usually a replication system to provide an expression vector for expression in the desired cellular host. For example, promoter sequences compatible with bacterial hosts are provided in plasmids containing convenient restriction sites for insertion of the desired coding sequence. The resulting expression vectors are transformed into suitable bacterial hosts. Of course, yeast or mammalian cell hosts may also be used, employing suitable vectors and control sequences.

2. Antigenic Determinants

An antigenic determinant may be administered with the PADRE peptides of the invention, either linked or admixed with the PADRE peptide, to elicit or enhance an immune response. CTL and carbohydrate epitopes from a number of immunogenic biomolecules can be used in the conjugates of the present invention. The particular immunogen used (e.g., polysaccharides, proteins, glycoproteins, lipids, glycolipids, lipopolysaccharides and the like) is not critical to the invention. For a listing of suitable immunogens for use in the present invention, e.g., BioCarb Chemicals Catalogue; and *The Jordan Report: Accelerated Development of Vaccine* 1995 NIH, Bethesda, Md., 1995).

Examples of suitable immunogens include those derived from bacterial surface polysaccharides which can be used in carbohydrate-based vaccines. Bacteria typically express carbohydrates on their cell surface as part of glycoproteins, glycolipids, O-specific side chains of lipopolysaccharides, capsular polysaccharides and the like. Exemplary bacterial strains include *Streptococcus pneumonia, Neisseria meningitidis, Haemophilus influenza*, Klebsiella spp., Pseudomonas spp., Salmonella spp., Shigella spp., and Group B *streptococci*.

A number of suitable bacterial carbohydrate epitopes are described in the prior art (e.g., Sanders, et al. *Pediatr. Res.* 37:812–819 (1995); Bartoloni, et al. *Vaccine* 13:463–470 (1995); Pirofski, et al., *Infect. Immun.* 63:2906–2911 (1995) and International Publication No. WO 93/21948) and are provided below.

| 1: CARBOHYDRATES ASSOCIATED WITH HUMAN TUMORS: | |
|---|---|
| 1.1 The majority of tumors: | |
| Gaβ4GlcβCer | Lactosylceramid |
| 1.2 Melanoma: | |
| NeuAcα8NeuAcα3Galβ4GlcβCer | GD3 |
| 9-O-Ac-GD3 | |
| NeuAcα8NeuAcα3(GalNAcβ4)Galβ4GlcβCer | GD2 |
| 9-O-Ac-GD2 | |
| Lactonized forms of these | |
| 1.3 Colon cancer and other types of cancer: | |
| GalNAα-Ser(Thr)(glycoprotein) | Tn-antigen |
| NeuAcα6GalNAcα-Ser(Thr) | Sialyl-Tn-antigen |
| Galβ3GlcNAc | Type 1 chain |
| NeuAcα3Galβ3(Fucα4)GlcNAcβ | Sialyl-Lewis a |
| NeuAcα3Galβ3(Fucα4)[NeuAcα6]GlcNAcβ | Disialyl-Lewis a |
| Galβ3(Fucα4)GlcNAcβGalgβ3(Fucα4)GlcNAβ | Dimer Lewis a |
| NeuAcα3Galβ4(Fucα3)GlcNAcβ | Sialyl-Lewis x |
| Galβ4(Fucα3)GlcNAcβ3Galβ4(Fucα3)GlcNAcβ | Dimer Lewis x |
| Galβ4(Fucα3)GlcNAcβ3Galβ4(Fucα3)GlcNAcβ3 | |
| Galβ4(Fucα3)GlcNAcβ | Trimer Lewis x |
| NeuAcα3-Dimer Lewis x | |
| NeuAcα3-Trimer Lewis x | |
| NeuAcα6-Oligomer Lewis x | |
| Lactonized forms of these in the case of sialic acid | |
| 1.4 Lung cancer and other types of cancer: | |
| Galβ4GlcNAcβ3Galcβ4GlcNAcβ | i-antigen (rep. lactosamine) |
| Galβ3(Fucα4)GlcNAcβGalβ4(Fucαt3)GlcNAco | Lewis a-Lewis x |
| Fucαt2Galβ3GalNAcβ4(NeuAcα3)Galβ4GlcβCer | Fuc-GM1 |
| Lactonized forms of Fuc-GM1 | |
| 1.5 Burkitt's Lymphoma: | |
| Galα4Galβ4GlcβCer | Gb3 |
| 1.6 Breast cancer: | |
| Fucα2Galβ3GalNAcβ3Galα4Galβ4GlcβCer | Fuc-Globopenta |
| Tn-antigen | |
| Sialyl-Tn-antigen | |
| 1.7 Teratocarcinoma: | |
| NeuAcα3Galβ3GalNAcβ3Galα4Galβ4GlcβCer | Sialyl-Globopenta |
| Lactonized form of the above | |
| 2: CARBOHYDRATES ASSOCIATED WITH EXPERIMENTAL TUMORS: | |
| 2.1 Melanoma (hamster): | |
| NeuAcα3Galβ4GlcβCer | GM3 |
| GD3 | |
| 9-0-Ac-GD3 | |
| GD2 | |
| Lactonized forms of these | |
| 2.2 Melanoma mouse | |
| GM3 | |
| Lactonized GM3 | |
| 3: CARBOHYDRATES ASSOCIATED WITH INFECTIOUS AGENTS: | |
| Mannan from *Candida albicans* | |
| Polysaccharide isolates from *Mycobacterium bovis* strain BCG | |

| -continued | |
|---|---|
| Lipophosphoglycan from *Leishmania major* | |
| Antigenic polysaccharides from *Salmonelia typhimurium* | |
| 4: CARBOHYDRATES ASSOCIATED WITH HIV: | |
| Fucα2Galβ4(Fucα3)GlcNAcβ | Lewis y |
| GalNAcα3(Fucα2)Galβ3GlcNAcβ | Blood group A, |
| NeuAcα6GalNAcα-Ser(Thr) | Sialyl $T_n$ antigen |
| GalNAcα-Ser(Thr) | $T_n$ antigen |

An exemplary viral antigen includes those derived from HIV (e.g., gp120). Exemplary fungal antigens include those derived from *Candida albicans, Cryptococcus neoformans*, Coccidoides spp., Histoplasma spp., and Aspergillus spp. Parasitic antigens include those derived from Plasmodium spp., Trypanosoma spp., Schistosoma spp., Leishmania spp. and the like.

Exemplary carbohydrate epitopes include bur are not limited to the following: Galα1,4Galβ-(for bacterial vaccines); GalNAcα-(for cancer vaccines); Manβ1,2 (Manβ1,2)$_n$ Manβ-(for fungal vaccines useful against, for example, *Candida albicans*), where n=0→∞;

GalNAcβ1,4(NeuAcα2,3)Galβ1,4Glcβ-O-ceramide. (for cancer vaccines);

Galα1,2(Tyvα1,3)Manα1,4Rhaα1,3Galα1,2(Tyα1,3)Manα1,4Rha- and

Galα1,2(Abeα1,3)Manα1,4Rhaα1,3Galα1,2(Abeα1,3)Manα1,4Rhaα1,3Galα1,2

(Abeα1,3)Manα1,4Rha-(both of which are useful against, for example, Salmonella spp.)

The carbohydrates used in the present invention can be prepared according to standard procedures, known to those of skill in the art. Typically, the oligosaccharides are prepared from suitable monomeric sugars through the formation of glycosidic linkages or isolated from natural sources and modified as appropriate. For example, a β-glycosyl bond can be formed between one sugar bearing a 1-halo substituent and a second, suitably protected sugar having at least one unprotected hydroxyl group. Such transformation are typically carried out in the presence of silver carbonate ($Ag_2CO_3$) or silver triflate.

Alternatively and preferably, the glycosidic linkages can be formed by enzymatic means, using methods described WO 96/32492. Briefly, glycosyltransferases such as sialyltransferase can be utilized for the construction of specific glycosidic linkages.

A number of sialyltransferases are known to those of skill in the art. This enzyme transfers sialic acid (NeuAc) to a Gal with the formation of an α-linkage between the two saccharides. Bonding (linkage) between the saccharides is between the 2-position of NeuAc and the 3-position of Gal.

An exemplary α(2,3)sialyltransferase (EC 2.4.99.6) often referred to as sialyltransferase, transfers sialic acid to the non-reducing terminal Gal of a Galβ1→3Glc disaccharide or glycoside. See, Van den Eijnden, et al., *J. Biol Chem.*, 256:3159 (1981), Weinstein, et al., *J. Biol. Chem.*, 257:13845 (1982) and Wen, et al.,*J. Biol. Chem.*, 267:21011 (1992). Another exemplary α-2,3-sialyltransferase (EC 2.4.99.4) transfers sialic acid to the non-reducing terminal Gal of the disaccharide or glycoside. See, Rearick, et al., *J. Biol. Chem.*, 254:4444 (1979) and Gillespie, et al., *J. Biol. Chem.*, 267:21004 (1992). Further exemplary enzymes include Gal-β-1,4-GlcNAc α-2,6 sialyltransferase (See, Kurosawa, et al. *Eur. J. Biochem.* 219:375–381 (1994)).

One of skill in the art will understand that other glycosyltransferases can be substituted into similar transferase cycles as have been described in detail for the sialyltransferase. For instance, the glycosyltransferase can also be, for instance, glucosyltransferases, e.g., Alg8 (Stagljov, et al., *Proc. Natl. Acad. Sci.* USA 91:5977 (1994)) or Alg5 (Heesen, et al. *Eur. J. Biochem.* 224:71 (1994)). Suitable N-acetylgalactosaminyltransferases include α(1,3) N-acetylgalactosaminyltransferase, β(1,4) N-acetylgalactosaminyltransferases (Nagata, et al. *J. Biol. Chem.* 267:12082–12089 (1992) and Smith, et al. *J. Biol. Chem.* 269:15162 (1994)) and polypeptide N-acetylgalactosaminyltransferase (Homa, et al. *J. Biol. Chem.* 268:12609 (1993)). Suitable N-acetylglucosaminyltransferases include GnTI (2.4.1.101, Hull, et al., BBRC 176:608 (1991)), GnTII, and GnTIII (Ihara, et al., *J. Biolchem.* 113:692 (1993)), GnTV (Shoreiban, et al., *J. Biol. Chem.* 268:15381 (1993)), 0-linked N-acetylglucosaminyltransferase (Bierhuizen, et al., *Proc. Natl. Acad.* Sci. USA 89:9326 (1992)), and hyaluronan synthase. Suitable mannosyltransferases include α(1, 2) mannosyltransferase, α(1,3) mannosyltransferase, β(1,4) mannosyltransferase, Dol-P-Man synthase, OCh1, and Pmtl.

Other suitable glycosyltransferase cycles are described in Ichikawa, et al., *J. Am. Chem. Soc.* 114:9283 (1992), Wong, et al., *J. Org. Chem.* 57:4343 (1992), DeLuca, et al., *J. Am. Chem.* Soc. 117:5869–5870 (1995), and Ichikawa, et al., in *Carbohydrates and Carbohydrate Polymers*, Yaltami, ed. (ATL Press, 1993).

For the above glycosyltransferase cycles, the concentrations or amounts of the various reactants used in the processes depend upon numerous factors including reaction conditions such as temperature and pH, and the choice and amount of acceptor saccharides to be glycosylated. Because the glycosylation process permits regeneration of activating nucleotides, activated donor sugars and scavenging of produced pyrophosphate in the presence of catalytic amounts of the enzymes, the process is limited by the concentrations or amounts of the stoichiometric substrates discussed before. The upper limit for the concentrations of reactants that can be used in accordance with the method of the present invention is determined by the solubility of such reactants.

CTL peptides comprising the appropriate epitopes are synthesized and then tested for their ability to bind to MHC Class I molecules in assays using, for example, purified class I molecules and iodinated peptides and/or cells expressing empty class I molecules by, for instance, immunofluorescent staining and flow microfluorimetry, peptide-dependent class I assembly assays, and inhibition of CTL recognition by peptide competition. Those peptides that bind to the class I molecule are further evaluated for their ability to serve as targets for CTLs derived from infected or immunized individuals, as well as for their capacity to induce primary in vitro or in vivo CTL responses that can give rise to CTL populations capable of reacting with virally infected target cells or tumor cells as potential therapeutic agents.

The one or more CTL and/or antibody-inducing peptides may be administered with one or more pan DR peptides in a mixture which may or may not involve noncovalent associations between the peptides. For instance, one or more of the peptides may be lipidated. Alternatively, the peptides may be covalently linked to form a PADRE-antigenic determinant.

To facilitate the association of the antigenic determinant with the PADRE peptide, additional amino acids can be added to the termini of the peptides. The additional residues can also be used for coupling to a carrier, support or larger peptide, for reasons discussed herein, or for modifying the physical or chemical properties of the peptide or oligopeptide, or the like. Amino acids such as tyrosine, cysteine, lysine, glutamic or aspartic acid, or the like, can be introduced at the C- or N-terminus of the peptide or oligopeptide. In addition, the peptide or oligopeptide sequences can differ from the natural sequence by being modified by terminal-NH$_2$ acylation, e.g., by alkanoyl ($C_1$–$C_{20}$) or thioglycolyl acetylation, terminal-carboxy amidation, e.g., ammonia, methylamine, etc. In some instances these modifications may provide sites for linking to a support or other molecule.

As with the PADRE peptides, it will be understood that the antigenic determinants may be modified to provide other desired attributes, e.g., improved pharmacological characteristics, while increasing or at least retaining substantially all of the biological activity of the unmodified peptide. For instance, the peptides can be modified by extending, decreasing or substituting in the peptides amino acid sequences by the addition or deletion of amino acids on either the amino terminal or carboxy terminal end, or both, of peptides derived from the sequences disclosed herein. Usually, the portion of the sequence which is intended to substantially mimic a CTL or antibody stimulating epitope will not differ by more than about 20% from the sequence of the target antigenic protein, except where additional amino acids may be added at either terminus for the purpose of modifying the physical or chemical properties of the peptide for ease of linking or coupling, and the like. In situations where regions of the peptide sequences are found to be polymorphic among viral subtypes, it may be desirable to vary one or more particular amino acids to more effectively mimic differing phytotoxic T-lymphocyte epitopes of different viral strains or subtypes.

Within the peptide sequence regions identified by the present invention as containing CTL or antibody epitopes, e.g., HBV specific peptides, there are residues (or those which are substantially functionally equivalent) which allow the peptide to retain its biological activity, i.e., the ability to stimulate a class I-restricted cytotoxic T lymphocytic response against virally infected cells or cells which express viral antigens. These residues can be identified by single amino acid substitutions, deletions, or insertions. In addition, the contributions made by the side chains of the residues can be probed via a systematic scan with a specified amino acid (e.g., Ala). Peptides which tolerate multiple substitutions generally incorporate such substitutions as small, relatively neutral molecules, e.g., Ala, Gly, Pro, or similar residues. The number and types of residues which can be substituted, added or subtracted will depend on the spacing necessary between the essential epitopic points and certain conformational and functional attributes which are sought (e.g., hydrophobicity vs. hydrophilicity). If desired, increased binding affinity of peptide analogues to its MHC molecule for presentation to a CTL can also be achieved by such alterations. Generally, any spacer substitutions, additions or deletions between epitopic and/or conformationally important residues should employ amino acids or other moieties chosen to avoid steric and charge interference which might disrupt binding. Peptides which tolerate substitutions while retaining the desired biological activity may also be synthesized as D-amino acid containing peptides, as described above for PADRE peptides.

The peptides of the invention can be combined via linkage to form polymers (multimers), or can be formulated in a composition without linkage, as an admixture. Where a peptide is linked to an identical peptide, thereby forming a homopolymer, a plurality of repeating epitopic units are presented. For example, multiple antigen peptide (MAP)

technology can be used to construct polymers containing both CTL and/or antibody peptides and PADRE peptides. When the peptides differ, e.g., a cocktail representing different viral subtypes, different epitopes within a subtype, different HLA restriction specificities, or peptides which contain T helper epitopes, heteropolymers with repeating units are provided. In addition to covalent linkages, noncovalent linkages capable of forming intermolecular and intrastructural bonds are also contemplated.

B. Preparation of Conjugates

A variety of means of attaching the PADRE peptide to the antigenic determinant are possible. Ionic interactions are possible through the termini or through the ε-amino group of lysine. Hydrogen bonding between the side groups of the residues and the antigenic determinants are also possible. Finally, conformation interactions between the PADRE peptide and the antigenic determinant may give rise to a stable attachment.

As noted above, antigenic determinants may be covalently linked to the PADRE peptides to prepare conjugates of the invention. Particularly preferred antigenic determinant/PADRE peptide conjugates are linked by a spacer molecule or linker. Alternatively, the antigenic determinant may be attached to the PADRE peptide without a linker.

The spacer or linker is typically comprised of neutral molecules, such as, aliphatic carbon chains, amino acids or amino acid mimetics, which are substantially uncharged under physiological conditions and may have linear or branched side chains. A number of compositions and methods for linking various biomolecules are known to those of skill in the art. The particular method by which a PADRE peptide is covalently linked, for instance, to a carbohydrate epitope is not critical to the invention. Methods suitable for linking PADRE peptides to carbohydrate antigens are disclosed for instance in WO 93/21948.

A number of linkers are well known and are either commercially available or are described in the scientific literature. The linking molecules used in the present invention are preferably of sufficient length to permit the two portions of the molecule to interact independently and freely with molecules exposed to them. In the case of carbohydrate epitopes, the linking molecules are typically 1–50 atoms long. Typically, the linking molecules will be aryl acetylene, ethylene glycol oligomers containing 2–14 monomer units, diamines, diacids, amino acids, or combinations thereof Other suitable linkers include lipid molecules such as ceramide and amino acid residues to which a different carbohydrate moiety is linked through the amino acid side chain.

The particular linking molecule used may be selected based upon its chemical/physical properties. The linking molecule has an appropriate functional group at each end, one group appropriate for attachment to the reactive sites on the carbohydrate portion and the other group appropriate for attachment to the amino acid/peptide portion. For example, groups appropriate for attachment to the carbohydrate portion are carboxylic acid, ester, isocyanate, alkyl halide, acyl halide and isothiocyanate. Similar groups would be useful for attachment to the amino acid portion. Appropriate selection of the functional group will depend on the nature of the reactive portion of the amino acid or peptide.

In one group of embodiments, alkyl or alkylene groups will be useful as linking groups and will have 1 to 20 carbon atoms, with those containing 3 to 6 carbon atoms being particularly preferred. For instance, linkers comprising polyethylene glycol and related structures can be used. The term "polyethylene glycol" is used to refer to those molecules which have repeating units of ethylene glycol, for example, hexaethylene glycol (HO—$(CH_2CH_2O)_5$—$CH_2CH_2OH$). When the term "polyethylene glycol" is used to refer to linking groups, it would be understood by one of skill in the art that other polyethers or polyols could be used as well (i.e, polypropylene glycol or mixtures of ethylene and propylene glycols).

In another group of embodiments, the alkyl or alkylene linking groups will be perfluorinated, rendering them less susceptible to biological degradation see, U.S. Pat. No. 5,055,562. Particularly preferred linking groups will include aminocaproic acid, 4-hydroxy butyric acid, 4-mercapto butyric acid, 3-amino-1-propanol, ethanolamine, perfluoroethanolamine, and perfluorohydroxybutyric acid. In one group of embodiments, the two portions are linked via a polyethylene glycol moiety.

In the case of linkers between PADRE peptides and other peptides (e.g., a PADRE peptide and a CTL inducing peptide), the spacers are typically selected from Ala, Gly, or other neutral spacers of nonpolar amino acids or neutral polar amino acids. In certain preferred embodiments herein the neutral spacer is Ala. It will be understood that the optionally present spacer need not be comprised of the same residues and thus may be a hetero- or homo-oligomer. Preferred exemplary spacers are homo-oligomers of Ala. When present, the spacer will usually be at least one or two residues, more usually three to six residues. In other embodiments the PADRE peptide is conjugated to the CTL or antibody-inducing peptide, preferably with the PADRE peptide positioned at the amino terminus. The peptides may be joined by a neutral linker, such as Ala-Ala-Ala or the like, and preferably further contain a lipid residue such as palmitic acid or the like which is attached to alpha and epsilon amino groups of a Lys residue (($PAM)_2Lys$), which is attached to the amino terminus of the peptide conjugate, typically via Ser-Ser linkage or the like.

The CTL or antibody-inducing peptide may be linked to the PADRE peptide either directly or via a spacer either at the amino or carboxy terminus of the CTL peptide. The amino terminus of either the CTL or antibody inducing peptide or the PADRE peptide may be acylated. In addition, the CTL peptide/PADRE conjugate may be linked to certain alkanoyl ($C_1$–$C_{20}$) lipids via one or more linking residues such as Gly, Gly-Gly, Ser, Ser-Ser as described below. Other useful lipid moieties include cholesterol, fatty acids, and the like.

In some embodiments it may be desirable to include in the pharmaceutical compositions of the invention at least one component which assists in priming CTL. Lipids have been identified as agents capable of assisting the priming CTL in vivo against viral antigens. For example, steroids such as cholesterol, fatty acids such as palmitic acid residues can be attached to the sulfhydryl group of a cysteine residue, the alpha and epsilon amino groups of a Lys residue and then linked, e.g., via one or more linking residues such as Gly, Gly-Gly-, Ser, Ser-Ser, or the like, to an immunogenic peptide, such as a PADRE peptide. Alternatively, in place of fatty acids, long chain alkyl groups can be linked through an ether linkage to the final amino acid (e.g, a cysteine residue).

The lipidated peptide can be injected, either directly in a micellar form, incorporated into a liposome or emulsified in an adjuvant, e.g., incomplete Freund's adjuvant. In a preferred embodiment a particularly effective immunogen comprises palmitic acid attached to alpha and epsilon amino groups of Lys, which is attached via linkage, e.g., Ser-Ser, to the amino terminus of the immunogenic peptide.

As another example of lipid priming of CTL responses, *E. coli* lipoproteins, such as tripalmitoyl-S-glycerylcysteinlyseryl-serine ($P_3CSS$) can be used to prime virus specific CTL when covalently attached to an appropriate peptide. See, Deres, et al., *Nature* 342:561–564 (1989). Peptides of the invention can be coupled to $P_3CSS$, for example, and the lipopeptide administered to an individual to specifically prime a CTL response to the target antigen. Further, as the induction of neutralizing antibodies can also be primed with $P_3CSS$ conjugated to a peptide which displays an appropriate epitope, the two compositions can be combined to more effectively elicit both humoral and cell-mediated responses to infection.

In the case of PADRE peptides conjugated to carbohydrate epitopes, the lipid moieties may be linked to the opposite terminus of the carbohydrate (e.g., carbohydrate linked to the C-terminus and lipid linked to the N-terminus). Alternatively, both the lipid and the carbohydrate moieties may be linked to the same end of the peptide. For instance, the two moieties may be linked to the same linker on the N-terminus.

C. Pharmaceutical Compositions

The compounds of the present invention, and pharmaceutical and vaccine compositions thereof, can be administered to mammals, particularly humans, for prophylactic and/or therapeutic purposes. The present invention can be used to elicit and/or enhance immune responses against immunogens. For instance, CTL/PADRE mixtures may be used to treat and/or prevent viral infection and cancer. Alternatively, immunogens which induce antibody responses (e.g., carbohydrates) can be used. Examples of diseases which can be treated using the present invention include various bacterial infections, viral infections, fungal infections, parasitic infections and cancer.

In therapeutic applications, the present invention is administered to an individual already suffering from cancer, or infected with the microorganism of interest. Those in the incubation phase or the acute phase of the disease may be treated with the present invention separately or in conjunction with other treatments, as appropriate.

In therapeutic applications, a composition of the present invention is administered to a patient in an amount sufficient to elicit an effective CTL response or humoral response to the microorganism or tumor antigen and to cure, or at least partially arrest, symptoms and/or complications. An amount adequate to accomplish this is defined as "therapeutically effective dose." Amounts effective for this use will depend in part on the peptide composition, the manner of administration, the stage and severity of the disease being treated, the weight and general state of health of the patient, and the judgment of the prescribing physician.

Therapeutically effective amounts of the compositions of the present invention generally range for the initial immunization that is for therapeutic or prophylactic administration, from about 1.0 μg to about 10,000 μg of peptide for a 70 kg patient, usually from about 100 to about 8000 μg, and preferably between about 200 and about 6000 μg. These doses are followed by boosting dosages of from about 1.0 μg to about 1000 μg of peptide pursuant to a boosting regimen over weeks to months depending upon the patient's response and condition by measuring specific immune responses.

It must be kept in mind that the compositions of the present invention may generally be employed in serious disease states, that is, life-threatening or potentially life threatening situations. In such cases, in view of the minimization of extraneous substances and the relative nontoxic nature of the conjugates, it is possible and may be felt desirable by the treating physician to administer substantial excesses of these compositions.

Further, the present invention can be used prophylactically to prevent and/or ameliorate bacterial infections, viral infections, fungal infections, parasitic infections and cancer. Effective amounts are as described above. Additionally, one of ordinary skill in the vaccine arts would also know how to adjust or modify prophylactic treatments, as appropriate, for example by boosting and adjusting dosages and dosing regimes.

Therapeutic administration may begin at the first sign of disease or the detection or surgical removal of tumors or shortly after diagnosis in the case of acute infection. This is followed by boosting doses until symptoms are substantially abated and for a period thereafter. In chronic infection, initial high doses followed by boosting doses may be required.

Treatment of an infected individual with the compositions of the invention may hasten resolution of the infection in acutely infected individuals. For those individuals susceptible (or predisposed) to developing chronic infection the compositions are particularly useful in methods for preventing the evolution from acute to chronic infection. Where the susceptible individuals are identified prior to or during infection, for instance, as described herein, the composition can be targeted to them, minimizing need for administration to a larger population.

The present invention can also be used for the treatment of chronic infection and to stimulate the immune system to eliminate virus-infected cells in individuals with latent infections. It is important to provide an amount of compositions of the present invention in a formulation and mode of administration sufficient to effectively elicit and/or enhance an immune response. Thus, for treatment of chronic infection, a representative dose is in the range of about 1.0 μg to about 5000 μg, preferably about 5 μg to 1000 μg for a 70 kg patient per dose. Immunizing doses followed by boosting doses at established intervals, e.g., from one to four weeks, may be required, possibly for a prolonged period of time to effectively immunize an individual. In the case of chronic infection, administration should continue until at least clinical symptoms or laboratory tests indicate that the viral infection has been eliminated or substantially abated and for a period thereafter.

The pharmaceutical compositions for therapeutic or prophylactic treatment are intended for parenteral, topical, oral or local administration. Typically, the pharmaceutical compositions are administered parenterally, e.g., intravenously, subcutaneously, intradermally, or intramuscularly. Because of the ease of administration, the vaccine compositions of the invention are particularly suitable for oral administration. Thus, the invention provides compositions for parenteral administration which comprise a solution of the peptides or conjugates dissolved or suspended in an acceptable carrier, preferably an aqueous carrier. A variety of aqueous carriers may be used, e.g., water, buffered water, 0.9% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of compositions of the present invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

The present invention may also be administered via liposomes, which serve to target the conjugates to a particular tissue, such as lymphoid tissue, or targeted selectively to infected cells, as well as increase the half-life of the peptide composition. Liposomes include emulsions, foams, micelles, insoluble monolayers, liquid crystals, phospholipid dispersions, lamellar layers and the like. In these preparations the composition to be delivered is incorporated as part of a liposome, alone or in conjunction with a molecule which binds to, for example, a receptor prevalent among lymphoid cells. These molecules would include monoclonal antibodies which bind to the CD45 antigen, or with other therapeutic or immunogenic compositions. Thus, liposomes filled with a desired composition of the present invention can be directed to the site of lymphoid cells, where the liposomes then deliver the selected therapeutic/immunogenic peptide compositions. Liposomes for use in the invention are formed from standard vesicle-forming lipids, which generally include neutral and negatively charged phospholipids and a sterol, such as cholesterol. The selection of lipids is generally guided by consideration of liposome size, acid lability and stability of the liposomes in the blood stream. A variety of methods are available for preparing liposomes, as described in, e.g., Szoka, et al., *Ann. Rev. Biophys. Bioeng.* 9:467 (1980), U.S. Pat. Nos. 4,235,871, 4,501,728, 4,837,028, and 5,019,369, incorporated herein by reference.

For targeting to the immune cells, a ligand to be incorporated into the liposome can include antibodies or fragments thereof specific for cell surface determinants of the desired immune system cells. A liposome suspension containing a composition of the present invention may be administered intravenously, locally, topically, etc. in a dose which varies according to, inter alia, the manner of administration, the composition being delivered, and the stage of the disease being treated.

Alternatively, DNA or RNA encoding both one or more PADRE peptides and a polypeptide containing one or more CTL epitopes or antibody inducing epitopes may be introduced into patients to obtain an immune response to the polypeptides which the nucleic acid encodes. Wolff, et. al., *Science* 247: 1465–1468 (1990) describes the expression of polypeptides which nucleic acids encode.

For solid compositions, conventional nontoxic solid carriers may be used. These may include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, that is, one or more conjugates of the invention, and more preferably at a concentration of 25–75%.

For aerosol administration, the compositions of the present invention are preferably supplied in finely divided form along with a surfactant and propellant. Typical percentages of the composition are 0.01–20% by weight, preferably 1–10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1–20% by weight of the composition, preferably 0.25–5%. The balance of the composition is ordinarily propellant. A carrier can also be included, if desired, as with lecithin for intranasal delivery.

In another aspect, the present invention is directed to vaccines which contain as an active ingredient an immunogenically effective amount of a composition of the present invention as described herein. The compositions may be introduced into a host, including humans, linked to its own carrier or as a homopolymer or heteropolymer of active peptide units. Such a polymer has the advantage of increased immunological reaction and, where different peptides are used to make up the polymer, the additional ability to induce antibodies and/or CTLs that react with different antigenic determinants. Carriers are well known in the art, and include thyroglobulin, albumins such as bovine serum albumin, tetanus toxoid, polyamino acids such as poly (lysine:glutamic acid), hepatitis B virus core protein, hepatitis B virus recombinant vaccine and the like. The vaccines can also contain a physiologically tolerable (acceptable) diluent such as water, phosphate buffered saline, or saline, and further typically include an adjuvant. Adjuvants such as incomplete Freund's adjuvant, aluminum phosphate, aluminum hydroxide, or alum are materials well known in the art. And, as mentioned above, immune responses can be primed by conjugating compositions of the present invention to lipids, such as $P_3CSS$. Upon immunization with a composition as described herein, via injection, aerosol, oral, transdermal or other route, the immune system of the host responds by producing an enhanced immune response, humoral and/or cellular.

Vaccine compositions of the invention are administered to a patient susceptible to or otherwise at risk of disease, to elicit and/or enhance an immune response against an antigenic determinant. Such an amount is defined to be an "immunogenically effective dose," either for therapeutic or prophylactic use. In this use, the precise amounts again depend on the patient's state of health and weight, the mode of administration, the nature of the formulation, etc., but generally range from about 1.0 $\mu$g to about 5000 $\mu$g per 70 kilogram patient, more commonly from about 10 $\mu$g to about 500 $\mu$g per 70 kg of body weight.

In some instances it may be desirable to combine the compositions of the present invention with vaccines which induce neutralizing antibody responses to infections and cancers of interest.

The compositions of this invention may also be used to make monoclonal antibodies. Such antibodies may be useful as potential diagnostic or therapeutic agents.

The compositions of the present invention may also find use as diagnostic reagents. For example, a composition of the invention may be used to determine the susceptibility of a particular individual to a treatment regimen which employs the antigenic determinants, and thus may be helpful in modifying an existing treatment protocol or in determining a prognosis for an affected individual. In addition, the compositions of the present invention may also be used to predict which individuals will be at substantial risk for developing chronic infection.

The following examples are offered by way of illustration and not by way of limitation.

D. EXAMPLES

Example 1

Experimental Procedures a. Cell Lines and MHC Purification

Various cell lines were used as sources of purified human and mouse class II molecules. The following Epstein-Barr virus (EBV) transformed homozygous cell lines were used as sources of human HLA class II molecules (Valli, et al., *J. Clin. Invest.* 91:616–628, 1993): LG2 [DB1*0101 (DR1)]; 3107 [DRB1*1501 (DR2w2b)]; MAT [DRB1*0301 (DR3) DBR3*0101 (DR52a)]; PREISS [DRB1*0401 (DR4w4)]; BIN40 [DRB1*0404 (DR4w14)]; SWEIG [DRB1*11011 (DR5)]; PITOUT [DRB1*0701 (DR7)]; PF[DQA1*0301/DQB1*0310 (DQ3.1).

In some instances, transfected fibroblasts were used: L416.3 [DRB5*0101 (DR2w2a)]; TR81.19 [DRB3*0101 (DR52a)]; and L257.6 [DRB4*0101 (Drw53)].

For mouse class II molecules, the following cell lines were used: A20 ($IA^d$, $IE^d$) (Sette, et al., *Science* 258:1801–1804, (1992)); CH12 ($IA^k$, $IE^k$ (Sette, et al., 1992); LS102.9 ($IA^s$) (Wall, et al., *Int. Imm.* 4:773–777, (1992)); and DB27.4 ($IA^b$) (Wall, et al., *J. Immuno.* 152:4526–4536 (1994)).

b. Purification of MHC Molecules

MHC molecules were purified essentially as described (Gorga, et al., *J. Biol. Chem.* 262:16087–16094 (1987)). Briefly, human class II molecules were purified by affinity chromatography using the LB3.1 (all DR, Valli, et al., *J. Clin. Invest.* 91:616–628 (1993)) or the IVD 12 (DQ3.1, Sidney, et al., *J. Immunol.* 152:4516–4525 (1994)) monoclonal antibodies. Mouse class II molecules were purified by the use of the MKD6 ($IA^d$, Sette, et al., *Science* 258:1801–1804 (1992)); 10.3.6 ($IA^k$, Sette, et al., supra); 14.44 ($IE^d$ and $IE^k$, Sette, et al., supra); and Y3JP ($IA^s$, Wall, et al., *Int. Immunol.* 4:773–777 (1992)) monoclonal antibodies.

C. Peptide Synthesis

Peptides were synthesized by sequential coupling of N-α-Fmoc-protected amino acids on an Applied Biosystems (Foster City, Calif.) 430A peptide synthesizer using standard Fmoc coupling cycles (software version 1.40). All amino acids, reagents, and resins were obtained from Applied Biosystems or Nova Biochem (San Diego, Calif.). Solvents were obtained from Burdick & Jackson. Solid-phase synthesis was started from an appropriately substituted Fmoc-amino acid-Wang resin. The loading of the starting resin was 0.5–0.7 mmol/g polystyrene, and 0.1 or 0.25 meq were used in each synthesis. A typical reaction cycle proceeded as follows: The N-terminal Fmoc group was removed with 25% piperidine in dimethylformamide (DMF) for 5 min, followed by another treatment with 25% in DMF for 15 min. The resin was washed 5 times with DMF. A 4 to 10-fold excess of a preformed 1-hydroxybenzotriazole ester of the appropriate Fmoc-amino acid in an N-methylpyrolidone (NMP) solution of was added to the resin, and the mixture was allowed to react for 30–90 min. The resin was washed with DMF in preparation for the next elongation cycle. The fully protected, resin-bound peptide was subjected to a piperidine cycle to remove the terminal Fmoc group. The product was washed with dichloromethane and dried. The resin was then treated with trifluoroacetic acid in the presence of appropriate scavengers (e.g., 5% (v/v) in water) for 60 min at 20° C. After evaporation of excess trifluoroacetic acid, the crude peptide was washed with diethylether, dissolved in water, and lyophilized. The peptides were purified to >95% homogeneity by reverse-phase HPLC using $H_2O$/$CH_3CN$ gradients containing 0.8% TFA modifier on a Vydac, 300A pore-size, C-18 preparative column. The purity of the synthetic peptides was assayed on an analytical reverse-phase column and their composition ascertained by amino acid analysis and/or sequencing. The cyclohexylalanine used in the synthetic procedures was purchased from Nova Biochem (San Diego, Calif.). Palmitylated peptides were produced by coupling palmitic acid on the peptides bound to the resin before cleaving the peptide. Coupling was accomplished by a symmetrical anhydride method, i.e., twofold excess of palmitic acid and one-fold of diisopropylcarbodiimide in dichloromethane for 1 hour.

d. MHC Peptide Binding Assays

Purified mouse or human class II molecules (5 to 500 nM) were incubated with 5 nM $^{125}$I-peptides for 48 hours in PBS containing 5% DMSO in the presence of a protease inhibitor mixture. Purified peptides were iodinated using the chloramine-T method (Buus, et al., *Science* 235:1353–1358 (1987)). The final concentrations of protease inhibitors were: 1 nM PMSF, 1.3 mM 1.10 phenanthrolone, 73 μM pepstatin A, 8 mM EDTA, 6 mM N-ethylmaleimide, and 200 μM Nα-p-tosyl-L-lysine chloromethyl ketone. Final detergent concentration in the incubation mixture was 2.6% digitonin ($IA^d$ and $IA^k$) or 0.05% NP-40 (all other class II molecules). Class I-peptide complexes were separated from free peptide by gel filtration on Sephadex G-50 or TSK2000 columns, and the fraction of peptide bound to MHC class II molecules was calculated as previously described (Sette, et al., *J. Immunol.* 142:35–40 (1989)). In preliminary experiments, each of the DR preparations was titered in the presence of fixed amounts of iodinated peptides to determine the concentration of class II molecules necessary to bind 10 to 20% of the total radioactivity. All subsequent inhibition and direct binding assays were then performed using this class II concentration. In the inhibition assays, inhibitory peptides were typically tested at concentrations ranging from 120 μg/mL to 1.2 μg/mL. The data were then plotted, and the dose yielding 50% inhibition was measured. Each peptide was tested in two to four completely independent experiments.

As used herein binding at <50 nM constitutes high affinity and binding at 50–500 nM constitutes intermediate affinity binding.

e. Inhibition of DR Restricted Peptide Presentation

The capacity of peptides to block the antigen presenting function of MHC was assayed by incubating mitomycin C-treated EBV cells of the appropriate DR with inhibitor peptides in RPMI 1640 (Bio Whittaker, Walkersville, Md.) in complete medium containing 10% human serum (Gemini Bioproducts, Inc., Calabasas, Calif.). The inhibitor peptides were routinely titrated over a range of four ten-fold dilutions starting at a concentration of 150 μg/mL in 96-well U-bottom plates (Costar, Cambridge, Mass.) containing $5×10^4$ cells. Along with inhibitor peptide, assay wells also received suboptimal concentrations of the HA 307–319 peptide (DR1, DR4w4, DR5, DR52b) or HA 307–319, $Y_{309}>F$ (DR4w14), or Lol P1 171–190 (DR3) (Sidney, et al., *J. Immunol.* 149:2634–2640 (1992)), which, in the absence of inhibitor peptides, resulted in 30–50% of the maximal proliferative response. This concentration was routinely 50 to 200 μg/mL. After incubating APC with peptides for 2 hr at 37° C. in a 5% $CO_2$ incubator, $2\times10^4$ T cells were added to each well. The T cell clones used were Cl 1 (DR1 and DR52b (Krieger, et al., *J. Immunol.* 146:2331–2340 (1991))); Clone 42.19 (DRw14); Clone JK1 (DR5); and line 132–132 (DR3). The proliferation of the T cells was measured three days later. Briefly, 24 hours after T cell addition, [$^3$H]-thymidine (1 μCi/well) (ICN, Irvine, Calif.) was added to each well for a final 18 hr incubation. Cells were then harvested onto glass fiber filters (LKB Wallac cell harvester 1295–001, LKB, Gaithersburg, Md.), and thymidine incorporation (LKB betaplate counter 1205) was measured. The percent inhibition of antigen presentation was calculated for each dose of inhibitor peptide required to inhibit 50% of the proliferative response.

Example 2

DR Binding Specificity of "Universal" Peptide Epitopes

The binding motifs of several murine and human class II MHC alleles have been defined, and motif analysis by sequencing of naturally processed peptides has also recently been described for various class II types (Rudensky, et al., *Nature* 353:622–627 (1991); Chicz, et al., *Nature* 358:764–768 (1992); Hunt, et al., *Science* 256:1817–1820 (1992); and Rudensky, et al., *Nature* 359:429–431 (1992)).

In the case of DR molecules in particular, it has been shown (Brown, et al., *Nature* 364:33–39 (1993)) that a large hydrophobic anchor engaging a corresponding hydrophobic pocket of the MHC binding groove is the most crucial determinant of peptide-DR interactions. Several other anchors play definite, albeit less prominent roles and help determine allelic specificity. Recently it has also been emphasized that the peptide backbone of the C-terminal half of the peptide molecule is engaged in direct hydrogen bonding with the walls of the MHC binding groove.

Although the allele-specific polymorphic residues that line the peptide binding pockets of MHC tend to endow each allele with the capacity to bind a unique set of peptides, there are many instances in which a given peptide has been shown to bind to MHC molecules of different specificities. This has been best documented in the case of the human DR isotype, in which it had been previously noted that several DR alleles appeared to recognize similar motifs, and independently, several investigators reported degenerate binding and/or recognition of certain peptide epitopes in the context of multiple DR types, leading to the concept that certain peptides might represent "universal" epitopes (Busch, et al., *Int. Immunol.* 2:443–451 (1990); Panina-Bordignon, et al., *Eur. J. Immunol.* 19:2237–2242 (1989), Sinigaglia, et al., *Nature* 336:778–780 (1988); O'Sullivan, et al., *J. Immunol.* 147:2663–2669 (1991); Roache, et al., *J. Immunol.* 144:1849–1856 (1991); and Hill, et al., *J. Immunol.* 147:189–197(1991)).

The DR binding capacity of previously described peptides capable of binding more than one DR molecule (HA 307–319, Tr 830–843, CS 378–398, MT 17–31, and HBVnc 50–69 was established using the assay described in Example I, paragraph D. The data obtained (Table II, section A) demonstrate that although these peptides were indeed capable of binding several of the DR molecules tested, they failed to bind to others. For example, the HA 307–319 bound with high (<50 nM) or intermediate (50–500 nM) affinity to DR1, DR4w4, DR5, DR7, and DR2w2a, and weakly to DRw53 (2.2 μM); while no binding was detectable for the remaining four DR specificities. HBVnc 50–69 also bound five of the ten DR specificities tested (DR1, DR2w2b, DR4w4, DR5, and DR2w2a) with high or intermediate affinity. Tr 830–843 and CS 378–398 bound with high or intermediate affinity to four out of ten DR molecules tested (DR1, DR5, DR7, DR2w2a and DR1, DR4w4, DR5, DR7, respectively) and MT 17–31 bound with high or intermediate affinity to three out of ten of the DR types.

In conclusion, although these previously described "universal" epitopes bound to several DR types, they were not completely cross-reactive in their binding capacity, in that a maximum of 50% of the DR specificities tested bound a given peptide with high to intermediate affinity.

TABLE II

Binding Capacity of Various Peptide Epitopes to Different DR Alleles

| | | DRβ1 Alleles | | | | | | | | DRβ 2 Alleles | | SEQ ID |
|---|---|---|---|---|---|---|---|---|---|---|---|---|
| Peptide | Sequence | DR1 | DR2w2b | DR3 | DR4w4 | DR4w14 | DR5 | DR7 | DR52a | DRw53 | DR2w2a | NO: |
| A | | | | | | | | | | | | |
| HA 307–319 | PKYVKQNTLKLAT | 5(1) | —(2) | — | 45 | — | 118 | 385 | — | 2200 | 45 | 3 |
| TT 830–843 | QYIKANSKFIGITE | 52 | — | 3623 | — | — | 20 | 25 | — | — | 20 | 7 |
| CS 378–398 | DIEKKIAKMEKASSVFNVVNS | 17 | 1820 | — | 250 | 2272 | 154 | 147 | — | — | 1430 | 13 |
| MT (Y)17–31 | YSGPLKAEIAQRLEDV | 13 | — | — | — | — | — | 208 | 6266 | 6538 | 350 | 14 |
| HBVnc 50–69 | PHHTALRQAILCWGELMTLA | 70 | 9.1 | — | 85 | 505 | 263 | 676 | 2765 | ND (4) | 211 | 15 |
| B | | | | | | | | | | | | |
| 760.50 | aA(X)AAAKTAAAAa(3) | 3.1 | 569 | 6410 | 2.8 | 6.9 | 6.1 | 192 | 9400 | 560 | 57 | — |
| 760.57 | aA(X)AAAATLKAAa | 4.5 | 479 | 2550 | 2 | 3.1 | 5.4 | 78 | — | 3300 | 5 | — |

TABLE II-continued

Binding Capacity of Various Peptide Epitopes to Different DR Alleles

| | | DRβ1 Alleles | | | | | | | DRβ 2 Alleles | | | SEQ ID |
|---|---|---|---|---|---|---|---|---|---|---|---|---|
| Peptide | Sequence | DR1 | DR2w2b | DR3 | DR4w4 | DR4w14 | DR5 | DR7 | DR52a | DRw53 | DR2w2a | NO: |
| C | | | | | | | | | | | | |
| 906.09 | aA(X)VAAATLKAAa | 0.61 | 14 | 280 | 2.6 | 5.4 | 2.5 | 76 | 588 | 93 | 2.0 | — |
| 906.11 | aA(X)IAAATLKAAa | 0.38 | 19 | 100 | 2.8 | 3.3 | 2.4 | 31 | 1120 | 41 | 1.3 | — |
| D | | | | | | | | | | | | |
| 965.10 | aK(X)VAAWTLKAAa | 0.91 | 40 | 86 | 1.1 | 9.1 | 9.1 | 167 | 979 | 75 | 6 | — |
| 1024.03 | aKFVAAWTLKAAa | 1.2 | 27 | 1470 | 2 | 8 | 18 | 208 | 797 | 420 | 11 | — |

(1) nM IC50's values
(2) dashes indicat >10,000 nM
(3) X = cyclohexylalanine
(4) ND = not done Example 3

Development of Peptides with High Affinity for Multiple DR Alleles: 760.50 and 760.57

A number of peptides capable of binding with high affinity to the rheumatoid arthritis associated DR alleles DR1, DR4w4, and DR4w14 were generated. To produce these peptides, a strategy was used as initially described by Jardetzky, et al., *EMBO J.* 9:1797–1803 (1990), in which anchor residues that contain side chains critical for the binding to MHC are inserted into a poly-Alanine peptide of 13 residues(SEQ ID NO:15). Two such peptides, designated 760.50 and 760.57, which are described in copending parent application 08/121,101 were particularly interesting with regard to their broad DR binding specificity. When tested for binding to a panel of 10 purified DR molecules, it was found that, in general, these peptides bound with higher affinity and broader specificity than the natural "universal" epitopes described above (Table II, section B). Neither 760.50 nor 760.57 was completely cross-reactive, since only low affinity binding was detected in 4 of the 10 alleles analyzed (DR2w2b, DR3, DR52a, and DRw53).

Example 4

Development of Peptides with High Affinity for Multiple DR Alleles: 906–09 and 906.11

To further broaden specificity the 906.09 and 906.11 peptides were synthesized, in which a V or I was introduced at position 4 of the 760.57 peptide. As shown in Table II, section C, both 906.09 and 906.11 peptides retained the good binding affinity for DR1, DR2w2a, DR4, DR5, and DR7 (in the range of 0.3 to 80 nM). Furthermore, the binding capacity (in comparison to 760.50 and 760.57) for molecules DR2w2b, DR3, DR52a, and DRw53 was significantly improved (10- to 25-fold), with IC50 in the range of 20 to 1200 nM. Thus, nine of ten DR specificities tested bound these peptides with high or intermediate affinity, and one, DR52a, bound weakly.

In conclusion, these data illustrate the development of peptides binding with high affinity to most, if not all, DR alleles. Because of this broad cross-reactivity pattern amongst different DR molecules, we have determined that the 906.09 and 906.11 peptides are PADRE peptides.

Example 5

Pan DR Binding Peptides Also Bind DQ3.1 and Mouse Class II Molecules

Assays were carried out to determine whether the PADRE peptides were also capable of binding other human class II isotypes or non-human class II molecules. More specifically, the binding capacity of the PADRE peptides to DQ3.1 and several mouse class II specificities was determined, as shown in Table III. For reference purposes, the binding affinities of previously described mouse class II epitopes are also shown in Table III, section A. All of these previously described epitopes bound their relevant restriction elements with high or intermediate affinity, between 20 and 400 nM. It was found that, in general, the 760 series peptides (Table III, section B) bound with intermediate affinity, in the range of 80 to 700 nM, to five of the six alleles tested ($IA^b$, $IA^d$, $IE^d$, $IA^s$, $IE^k$. Interestingly, the 906 series peptides (Table III, section C) bound with significantly higher affinity, in the 10 to 100 nM range in the case of the alleles mentioned above, and 906.11 also bound with intermediate affinity to $IA^k$. With respect to binding to DQ3.1, it was found that 760.50, 760.57, 906.09, and 906.11 all bound with relatively high affinity to purified DQ3.1 molecules (in the 30 to 120 nM range).

As a control, the binding potential of the 760 and 906 peptides to human class I molecules was also examined. No binding was detected, up to 10 μM, to purified HLA-A1, -A2.1, -A3, -A11, and -A24 molecules (data not shown). In conclusion, these data suggest that the 906 series peptides are Pan class II (but not class I) MHC binding, peptides.

TABLE III

Capacity of Various Peptides to Bind Purified DQ3.1 and Mouse Class II MHC

| Peptide | Restriction Element | Sequence | Class II Alleles | | | | | | | SEQ ID NO: |
|---|---|---|---|---|---|---|---|---|---|---|
| | | | DQ3.1 | $IA^b$ | $IA^d$ | $IE^d$ | $IA^s$ | $IA^k$ | $IE^k$ | |
| A | | | | | | | | | | |
| $HBV_c$ 128–140 | $IA^b$ | TPPAYRPPNAPIL | $ND^a$ | 255 | — | — | — | — | — | 16 |
| Ova 323–336 | $IA^{d,b}$ | ISQAVHAAHAEINE | $577^b$ | 400 | 110 | — | 1038 | 1000 | 700 | 9 |
| λ rep. 12–26 | $IE^{d,k}$ | YLEDARRLKAIYEKKK | $—^c$ | — | 1100 | 170 | — | — | 28 | 10 |
| PLP 139–151 | $IA^s$ | HSLGKWLGHPDKF | — | >3100 | — | — | 86 | — | — | 17 |
| HEL46–61 | $IA^k$ | NTDGSTDYGILQINSR | 3750 | 7000 | 1222 | 8500 | — | 20 | — | 18 |
| B | | | | | | | | | | |
| 760.50 | | aA(X)AAAKTAAAAa | 31 | 200 | 688 | 155 | 491 | 10,000 | 127 | — |
| 760.57 | | aA(X)AAAATLKAAa | 94 | 377 | 192 | 172 | 120 | 5260 | 78 | — |
| C | | | | | | | | | | |
| 906.09 | | aA(X)VAAATLKAAa | 48 | 31 | 38 | 31 | 104 | 1333 | 11 | — |
| 906.11 | | aA(X)IAAATLKAAa | 115 | 28 | 25 | 13 | 98 | 154 | 14 | — |
| D | | | | | | | | | | |
| 965.10 | | aK(X)VAAWTLKAAa | 25 | 94 | 733 | 354 | 613 | 3333 | 326 | — |
| 1024.03 | | aKFVAAWTLKAAa | 23 | 44 | 3056 | 1133 | 1059 | — | 3500 | — |

[a]ND, not determined
[b]nM IC50's values
[c]—, no detectable binding (>10,000 nM)

Example 6

Inhibition of T Cell Proliferation by Pan DR Binders

Because of their degenerate class II binding capacity, the PADRE peptides are candidates as therapeutics in the inhibition of T cell mediated events involved in allograft rejection, allergic responses, or autoimmunity. Accordingly, the capacity of these peptides to block an antigen-specific in vitro T cell proliferative response was evaluated. The inhibition of antigen presentation assay described in Example 1, paragraph E was used to make these evaluations.

In keeping with their MHC binding capacity, it was found that these peptides were potent inhibitors of the proliferative responses of human T cells restricted by at least six different DR molecules (Table IV). More specifically, peptides 760.50 and 760.57, which have high binding affinities for DR1, DR4w4, DR4w14, and DR5, inhibited T cell proliferation restricted by those alleles, with IC50 in the 1.0 to 25 μm range. By contrast, these peptides bound DR3 molecules only weakly, in the 2.5 to 6.5 μM range, and accordingly, DR3 restricted T cell activation was inhibited poorly (IC50 of 220 μM for 760.57) or not at all (IC50 of >250 μM for 760.50).

The 906.09 and 906.11 peptides also inhibited DR1, DR4w4, DR4w14, and DR5 responses quite effectively (IC50 in the 0.5 to 15 μM range). As expected, the 906 analogs, which have intermediate DR3 binding capacity, were also capable of inhibiting DR3 restricted antigen presentation, with IC50 in the 30 to 60 μM range.

In the same set of experiments, we also tested the 760 and 906 peptides for their capacity to inhibit a DR52b restricted response. This experiment was of interest inasmuch as there is not a molecular binding assay to measure peptide binding to DR52b molecules. The data obtained demonstrate that both 906.09 and 906.11 peptides inhibited the presentation of HA 307–319 Clone 1 in the context of DR52b molecules with good IC50, in the 1 to 2 μM range, thereby extending to an eleventh allele the PADRE capacity of these peptides.

Finally, these peptides failed to inhibit proliferation of the HA-specific, DR-restricted T cell clone in response to the polyclonal mitogen PHA, and also failed to inhibit in the recently described T cell antagonist assay (De Magistris, et al., *Cell* 68:525–634 (1992)), in which peptides are added subsequent to (not simultaneously with) the antigenic stimulus (data not shown). These findings rule out the possibility that the results described above might have been caused by some non-specific cytotoxicity of the 760 or 906 peptides.

TABLE IV

Inhibition of T Cell Proliferation by Pan DR Binding Peptides

| PEPTIDE | SEQUENCE | Inhibition of antigen presentation: (50% μM inhibitory concentration) | | | | | |
|---|---|---|---|---|---|---|---|
| | | DR1 | DR3 | DR4w4 | DR4w14 | DR5 | DR52b |
| 760.50 | aA(X)AAAKTAAAAa | 4.3 | >250 | 3.2 | 2.8 | 25 | >180 |
| 760.57 | aA(X)AAAKTLKAAa | 2.1 | 220 | 0.94 | 0.79 | 18 | 7.5 |
| 906.09 | aA(X)VAAATLKAAa | 0.88 | 31 | 0.58 | 0.43 | 11 | 1.6 |
| 906.11 | aA(X)IAAATLKAAa | 1 | 56 | 0.74 | 0.59 | 13 | 1.7 |

Example 7

Generation of Pan DR T Cell Epitopes by Modification of Broadly Reactive Class II Binding Peptides PADRE peptides were used to produce Pan DR restricted T helper epitopes that could provide help for both humoral and cytotoxic responses. Because all of the potential TCR contact residues in the PADRE peptides were alanines, it was hypothesized that due to the limited interactions the methyl side chains could participate in, introduction of more bulky hydrophobic charged residues might improve the likelihood of interactions with T cell receptors and thereby increase their immunogenicity.

Following this line of reasoning, the 906.09 Pan DR peptide was further modified. Several analogs were generated by introducing bulky or charged side groups at positions 2, 5, and 7, which are potential TCR contact residues based on previous analysis of the HA 307–319 peptide. By contrast, those positions known to influence DR binding were left undisturbed (3, 4, 8, 9, and 11). In addition, analogs were also generated that carried the natural amino acid, Phe, instead of cyclohexylalanine at position 3. These peptides were then tested for retention of their capacity to bind multiple DR alleles, and those peptides that had no significant decrease in their DR binding capacity were then tested for their capacity to induce an immune response. The data from two of the best peptides, 965.10 and 1024.03, are discussed below.

When these two peptides were tested for HLA DR and murine Ia binding (Table II, section D and Table III, section D), it was found that, in general, they retained the high binding capacity and broad reactivity associated with the parent peptide, 906.09, for most DR alleles. The exceptions to this were represented by 1024.03 binding only weakly to DR3 (1470 nM) and also binding with intermediate (420 nM) rather than high affinity to DRw53. Also, the 965.10 and 1024.03 peptides showed greatly reduced binding capacities for most of the murine class II molecules tested. Good binding capacity was retained, however, for the $1A^b$ allele, thus allowing $H-2^b$ mice to be used to test the in vivo immunogenicity of these peptides (see below). Finally, good DQ3.1 binding capacity of both peptides (in the 25 nM range) was also retained.

Example 8

In Vitro Immunogenicity of PADRE Peptides

The Pan DR epitope 965.10, along with two of its progenitor peptides, 906.09 and 760.50 and the previously described natural epitope, TT 830–843, were compared for their capacity to stimulate in vitro T cell responses in peripheral blood mononuclear cells (PBMC) from normal individuals. The protocol used entailed repeated stimulation of peripheral blood lymphocytes (PBL) with autologous APC and peptide antigens, and was specifically designed to allow the study of primary in vitro responses. This protocol is provided below, followed by the results of the assays.

a. Assay Protocol

PBMC from healthy donors were stimulated in vitro using a protocol adapted from Manea, et al., *J. Immunol.* 146:1964–1971 (1991). PBMC were purified over Ficoll-Paque (Pharmacia LKB, Uppsala, Sweden) and plated in 4 wells of a 24-well tissue culture plate (Costar, Cambridge, Mass.) at $4 \times 10^6$ PBMC/well. The peptides were added at a final concentration of 10 µg/mL. Cultures were then incubated at 37° C., 5% $CO_2$. On day 4, recombinant IL-2 was added at a final concentration of 10 µg/mL. Cultures were routinely fed every three days thereafter by aspirating off 1 mL of media and replacing it with fresh medium containing IL-2.

T cells ($3 \times 10^5$/well) were stimulated with peptide (10 µg/mL) using autologous PBMC cells ($2 \times 10^6$ irradiated (7500 rad)/well) as antigen presenting cells in a total of 3 wells of a 24-well tissue culture plate. Two additional stimulations of the T cells with antigen were performed on approximately days 14 and 28. In addition, on days 14 and 28, T cell proliferative responses were determined as follows: $2 \times 10^4$ T cells/well; $1 \times 10^5$ irradiated PBMC/well as APC; the peptide concentration was titrated between 0.01–10 µg/mL final concentration in U-bottom 96 well tissue culture plates (Costar, Cambridge, Mass.). The T cell proliferation assays were harvested on day three as described above.

b. Results

Representative data from three normal donors are shown in FIG. 1. The data obtained following two rounds of stimulation are shown in panels A to C, and after a third round of stimulation, in panels D to F. As predicted, the parental peptides 760.50 and 906.09 were poorly immunogenic in these experiments. Neither peptide induced a significant (>10,000 cpm) response following two rounds of stimulation. After a third round of stimulation, 760.50 induced a response in one donor of the three tested. The natural "universal" epitope TT 830–843 also failed to give a significant response after two rounds of stimulation, and after the third round of stimulation, T-F 830–843 also generated a modest positive response in all three donors. In contrast to these weak responses, all three donors responded briskly after only two rounds of stimulation to the modified Pan DR peptide 965.10.

Figure 2:
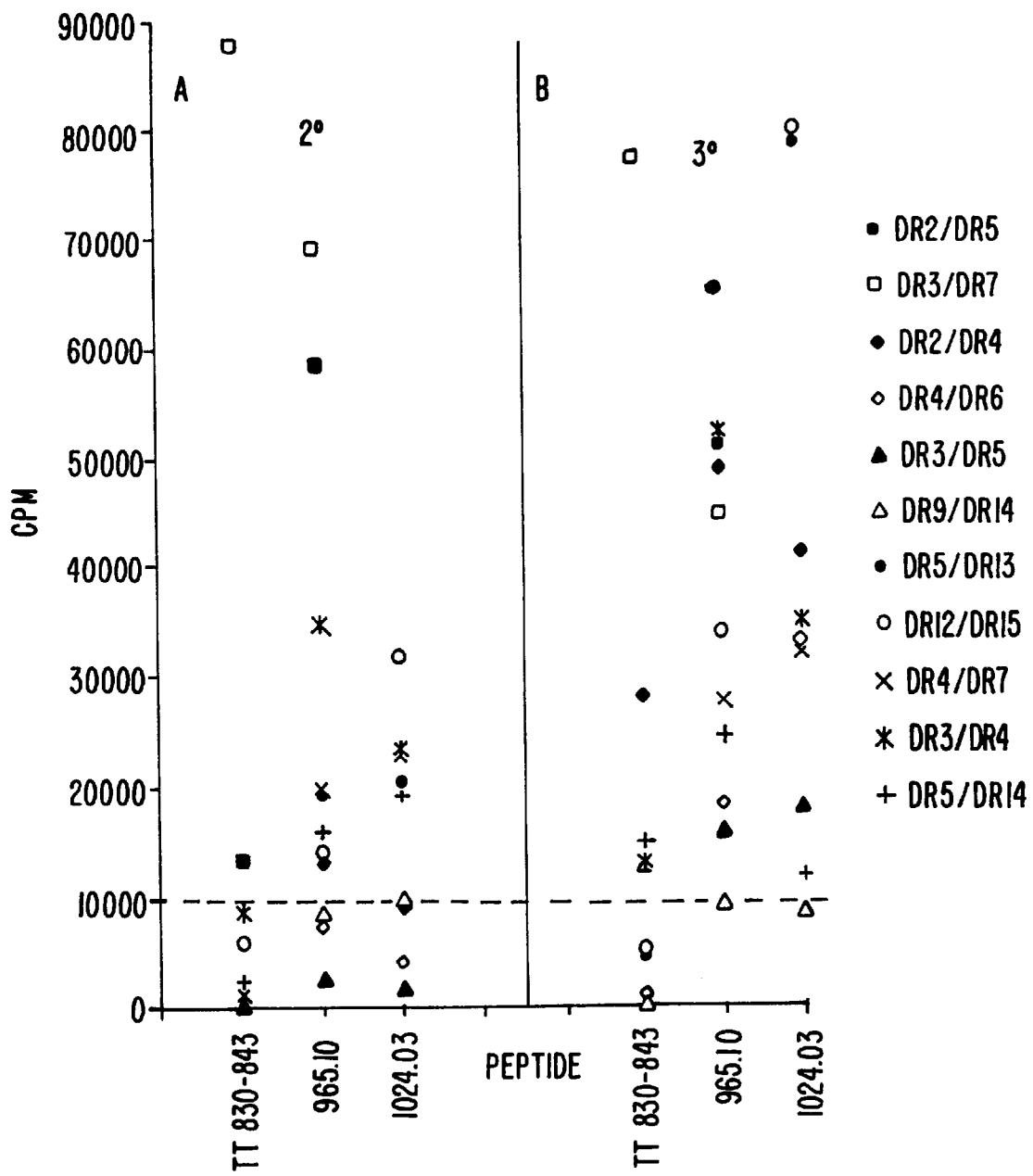
FIGS. 2A, 2B show summaries of antigen specific T cell responses from human PBMC.

FIGS. 2A and 2B summarize all the in vitro stimulation data that had been obtained in the first series of experiments (second and third stimulations, respectively). After two in vitro stimulations (FIG. 2A), peptide 965.10 was the only peptide able to significantly stimulate T cells in the majority of donors (9/12). TT 830–843 was able to generate a response in fewer individuals (3/12), while 760.50 and 906.09 both failed to stimulate any response (0/3). By the third stimulation (FIG. 2B), 965.10 generated significant responses in 11 of 12 donors tested, the TT 830–843 was now able to mount a significant response in a majority of the donors (7/12); 760.50 induced a response in 1 of 3 donors, and 906.09 failed to stimulate any of the 3 donors tested.

Figure 3:
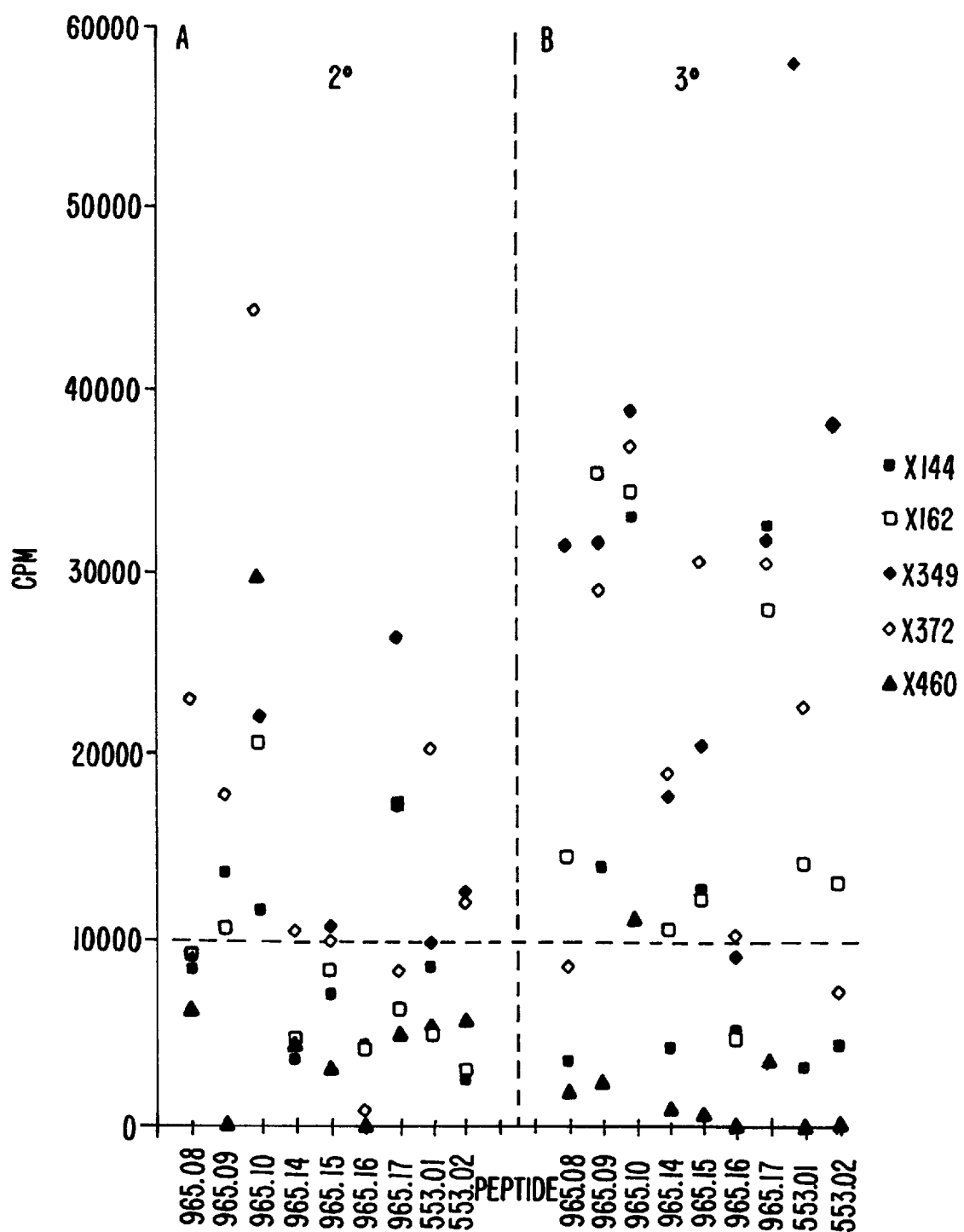
FIGS. 3A, 3B show summaries of antigen specific T cell responses from human PBMC.
Figure 4A:
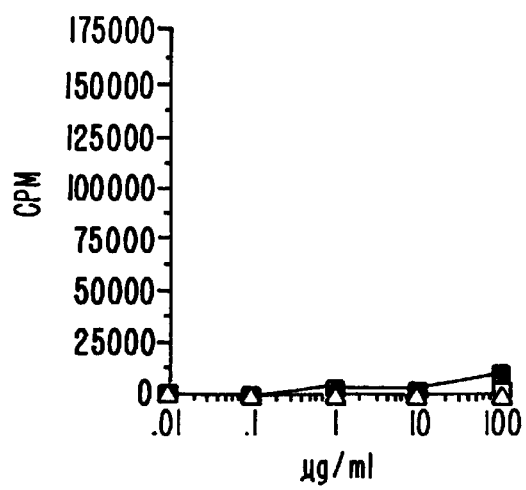
FIGS. 4A–4F show in vivo immunogenicity of various peptide epitopes as measured by proliferative capacity of primed murine lymph node T cells. C57BL/6J mice were injected with 20 μg/mouse (open triangle), 1 μg/mouse (closed square), 50 ng/mouse (open square), 2.5 ng/mouse (closed circle), or 0.125 ng/mouse (open circle) of TT 830–843 (FIG. 4A), Ova 323–336 (FIG. 4B), $HBV_c$ 128–140 (FIG. 4C), 965.10 (FIG. 4D) 1024.03 (FIG. 4E), and 760.50 (FIG. 4F). Ten days later, draining lymph nodes were removed and T cell proliferation assays performed as described in detail below. A representative of two independent experiments is shown.
Figure 4B:
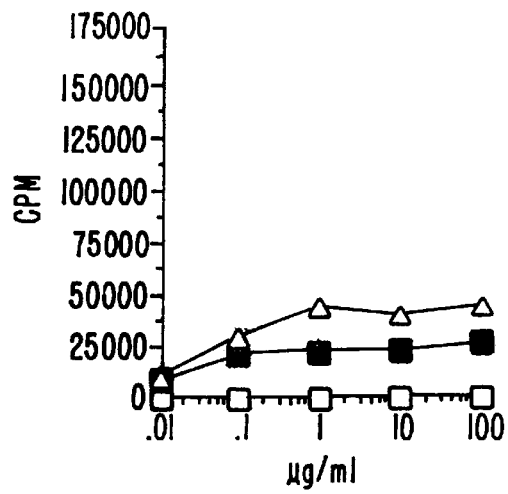
Figure 4C:
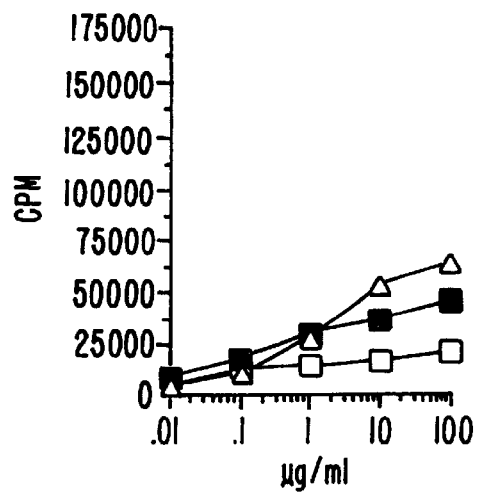
Figure 4D:
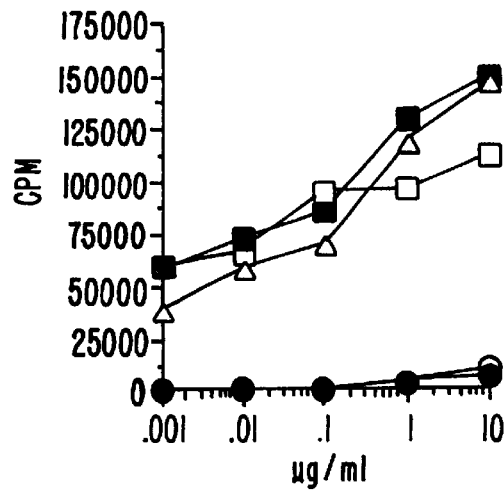
Figure 4E:
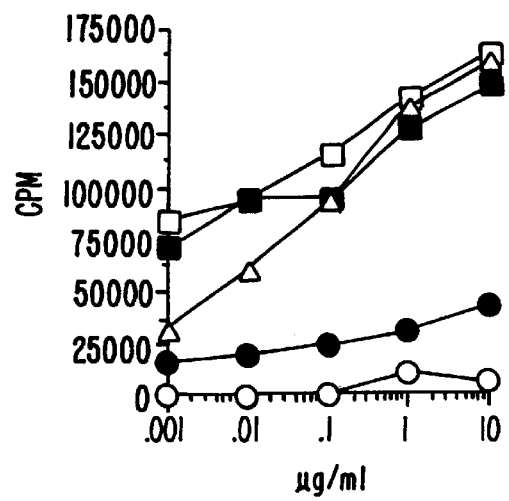
Figure 4F:
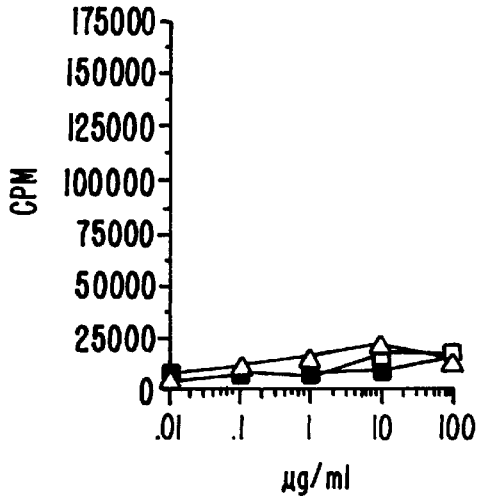

In our next series of experiments, analogs of 965.10 were examined for their ability to induce growth of PBMC. After two in vitro stimulations (FIG. 3A), peptide 965.10 was the only peptide able to induce the growth of PBMC cultures above background (10,000 cpm) in all 5 individuals tested. The analogs were, however, successful for a few individuals (965.08 (1/5), 965.09 (4/5), 965.14 (1/5), 965.15 (2/15), 965.16 (0/5), and 965.17 (2/5)). By the third stimulation (FIG. 3B), 965.10 maintained the capacity to induce the growth of PBMC cultures in all 5 individuals. Again the analogs had limited success (965.08 (2/5), 965.09 (4/5), 965.14 (3/5), 965.15 (4/5), 965.16 (1/5), and 965.17 (4/5)). However, two analogs, 965.09 and 965.17, were able to induce the growth of PBMC cultures in 4/5 individuals. It should be noted that as in the previous example, 965.10 was superior to TT 830–843 (553.01) in inducing growth in PBMC cultures.

The ability of 965.10 to induce the growth of specific T cell populations in vitro as early as the second stimulation, plus its ability to give a significant T cell response in virtually all of the donors by the third stimulation, demonstrates the superior immunogenic capacity of this peptide relative to peptides TF 830–843, 760.50 or 906.09, 965.08, 965.09, 65.14, 965.15, 965.16, 967.17, or 553.02.

Example 9

In Vivo Immunogenicity of the Pan DR Epitopes in Mice

The in vivo immunogenicity of the 760.50, 965.10, and 1024.03 peptides was tested in C57BL/6J (H-$2^b$+) mice.

To carry out these assays, C57BL/6J mice were injected subcutaneously at the base of the tail with a dose titration of various peptides (0.000125, 0.0025, 0.05, 1, and 20 μg/mouse) in PBS/CFA (Difco, Detroit, Mich.) in a 100 μl volume. On day 10, inguinal and paraaortic lymph nodes from groups of three mice/peptide dose were collected, pooled, and homogenized into single cell suspensions. Cells were washed two times and subsequently plated ($1 \times 10^6$ cells/well) in 96-well microtiter tissue culture plates. A log dose peptide titration (0.01 to 100 μg/mL) of the immunizing peptide was added and a standard three day T cell proliferation assay performed as described above.

In these experiments, the activity of the non-natural epitopes to two other previously defined natural $IA^b$ restricted epitopes, Ova 323–336 and HBV core 128–140, were compared. These two natural epitopes bound with a somewhat lower (3 to 14 fold) affinity than 965.10 (Table III, section A). The TT 830–843 peptide, which did not bind $IA^b$ appreciably (data not shown), was included as a negative control.

As shown in FIG. 4, panel A, it was found that, consistent with its inability to bind $IA^b$, TT 830–843 was unable to generate a specific T cell proliferative response. The known $IA^b$ restricted helper epitopes Ova 323–336 (FIG. 4, panel B) and HBVc 125–140 (FIG. 4, panel C) induced responses in the 25,000 to 70,000 cpm range at the two highest peptide doses used for immunization (1 and 20 μg/mouse). The Pan DR epitopes 965.10 (FIG. 4, panel D) and 1024.03 (FIG. 4, panel E) stimulated the strongest responses, with effective immunizing doses being obtained with as little as 0.05 μg/mouse, with a magnitude in the 100,000 to 150,000 cpm range. In contrast, peptide 760.50 (FIG. 4, panel F) was only marginally immunogenic, with a very weak proliferative response being induced, and only at the highest (20 μg/mouse) dose tested. These results indicate that the Pan DR epitopes 965.10 and 1024.03 function as highly effective helper epitopes in vivo, as well as in vitro. Together with the human immunogenicity data, they also suggest that in addition to high MHC binding capacity, the presence of "immunodominant" amino acid residues at potential TCR contact positions is an important element for the generation of vigorous T cell responses.

Example 10

Pan DR Peptides Act as Helper Epitopes For In Vivo CTL Induction in Mice

It is generally assumed that the capacity to induce a T cell proliferative response is an indicator of the helper capacity of a peptide epitope. We sought to verify this by measuring the capacity of the 965.10 peptide to deliver help in the generation of a CTL response. The CTL induction experiments were carried out according to the protocol provided below.

a. CTL Induction Protocol

Groups of 3–6 C57BL/6J mice were immunized by subcutaneous injection at the base of the tail with a mixture of a lipidated CTL epitope (dipalmitoylated Ova 257–264) and a helper epitope dissolved in phosphate-buffered saline, 5% DMSO. After 11 days, mice were sacrificed and splenocytes ($3 \times 10^7$/10 mL/T25 flask) were stimulated in vitro by the addition of Ova 257–264 (1 μg/mL) and incubated for 6 days. Cytotoxicity was measured using $^{51}$Cr labeled EL4 target cells, which were incubated at 37° C. for 1 hour with the CTL epitope peptide. $^{51}$Cr-labeled target cells ($10 \times 10^4$) were added to varying numbers of effector cells in U-bottomed 96-well plates and $^{51}$Cr release was measured after 6 hours. Data are expressed in lytic units/$10^6$ effector cells. One lytic unit is defined as the number of lymphocytes required to achieve 30% lysis of $1 \times 10^4$ $^{51}$Cr labeled target cells.

b. Results

The results obtained are shown in Table V. It was found that the Pan DR epitope 965.10 induced a CTL response in a dose-dependent fashion, with an optimum of 307 lytic units observed when 5 nmoles/mouse of 965.10 peptide was co-injected with the lipidated Ova 257–264 CTL epitope. In contrast, the helper activity of the Ova 323–336 and HBVC 128–140 epitopes was much less pronounced, both in terms of the magnitude of the helper effect (four-fold and three-fold increase, respectively) and of the dose required for induction of optimal helper activity (100 nM/mouse).

TABLE V

Helper Activity of $IA^b$ Restricted Epitopes in CTL Induction

| T Helper Peptide | Optimal Dose of Helper Peptide (nmoles/Mouse) | CTL Response (A Lytic Units/ 106 Cells) |
|---|---|---|
| — | — | 12 +/− 2 |
| Ova 323–336 | 100 | 50 +/− 5 |
| HBV core 128–140 | 100 | 35 +/− 10 |
| 965.10 | 5 | 307 +/− 55 |

Example 11

Induction of Antibodies by PADRE Peptides a. Materials and Methods i. Linear Constructs The constructs utilized were mainly based on a dimer of the nine amino acid residue repeat from the repeat region of the recombinant *Plasmodium vivax* CS which contains approximately 60% of the CS protein sequence. This peptide (sequence GDRADGQPAGDRADGQPA, referred to as a $B_2$ peptide SEQ ID NO:19) was shown to be immunogenic in mice of the H-2k and H-2a haplotypes (Nardin, et al., *Eur. J. Immunol* (1988)), but not of the d or b haplotypes.

In addition to the $B_2$ peptides, we have also used in our experiments two constructs in which the $B_2$ was covalently linked via its N-terminus to either the PADRE 965.10 peptide (sequence aK(X)VAAWLKAa; x=Cyclohexylamine) or the control $IA_b$-restricted helper epitope OVA 323–336 (sequence ISQAVHAAHAEINIE SEQ ID NO:9).

ii. Polyvalent Constructs

It had previously been shown that synthetic vaccines containing sequences which correspond to monovalent immunodominant B cell epitopes, induce only low antibody response and no appreciable protective effect, either by themselves or when coupled to monovalent helper epitopes Based on these results, recent vaccine designs have focused on the simultaneous incorporation of both multiple B cell epitopes and T helper (Th) epitopes (Tam, et al., *J. Exp. Med.* 171:229–306 (1990)). The development of the multiple-antigen peptide (MAP) technology (Tam, J. P., *Proc. Natl. Acad. Sci.* USA 85:5409–5413 (1988)) provides a mean to design such constructs containing both T helper epitopes and multiple B cell sites. Three MAP constructs were used.

iii. Immunizations

C57B16 (H-2$^b$) mice were injected at the base of the tail with 100 μg of peptide in 100 μl of CFA and bled 4 weeks later. They were subsequently boosted with the same amount of peptide in 100 μl of IFA and bled again 2 weeks later. Antibody titers (primary and secondary response) were measured using an ELISA assay using plates coated with 0.1 μg/well of B$_3$ peptide (sequence GDRADGQPADGDRADGQPAGDRADGQPA SEQ ID NO:20). B10A mice (H-2k) were used as a positive control for anti-B2 peptide response.

B$_2$ MAP4:

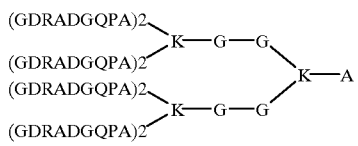

OVA B$_2$ MAP4:

PADRE B$_2$ MAP4:

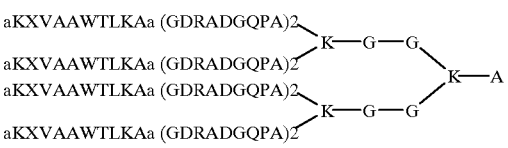

iv. Elisa

A standard ELISA was performed using (GDRADGQPA SEQ ID NO:20)$_3$ as the coating peptide.

b. Results

The results obtained (Table VI) show that B10A mice responded very well to the B2 peptide. Similar levels of primary response were observed with either the B$_2$ or B$_2$ MAP 4 constructs. Boosting increased the response to the multivalent B$_2$ MAP 4 about 10 fold, but not to the monovalent B$_2$ antigen.

In the case of H-2b mice, no response was observed with either B$_2$ or B$_2$ MAP 4, either after a single injection or boosting. The MAP constructs which included the OVA or PADRE helper epitopes were remarkably effective, yielding titers in the 1 to 3×10$^5$ range after a single injection and in the 3 to 8×10$^5$ range after the boost.

Even the monovalent constructs were somewhat effective if T cell help was provided. The OVA B$_2$ constructs reached titers in the 3×10$^4$ range (either after one or two injections). Most interestingly, titers of 6×10$^4$ and 3.7×10$^5$ were obtained in even response to the monovalent PADRE B$_2$ constructs.

TABLE VI

| Treatment | Mice | |
|---|---|---|
| | B10A(H-2k) | BL6(H-2b) |
| Primary Response | | |
| B$_2$ | 101675*/1.77[1] | 776/1.8 |
| OVA B$_2$ | ND2 | 31963/4.7 |
| PADRE-B$_2$ | ND | 62764/1.54 |
| B$_2$MAP4 | 75755*/1.77 | 90/1.3 |
| OVA-B$_2$-MAP4 | ND | 257306/3.4 |
| PADRE-B$_2$-MAP4 | ND | 130113/2.14 |
| Secondary Response | | |
| B$_2$ | 93364*/1.4 | 107/1.34 |
| OVA-B$_2$ | ND | 37443*/1.8 |
| PADRE-B$_2$ | ND | 370334/3.25 |
| B$_2$-MAP4 | 1012119/2.3 | 155/1.17 |
| OVA-B$_2$-MAP4 | ND | 333850/1.78 |
| PADRE-B$_2$-MAP4 | ND | 749979/1.79 |

Results expressed in geometric mean
*/Standard deviation of titers from groups of 3 to 6 individual mice.
ND indicates Not Done.

c. Conclusion

In conclusion, these experiments demonstrate that PADRE peptides can be utilized to raise powerful antibody responses. Because of their very broad spectrum of reactivity, it is anticipated that use of PADRE peptides should allow for coverage of a very high fraction of the human population, higher than the one covered by either "universal" T cell epitopes. In certain cases, the use of PADRE could also allow the use of simplified constructs, with favorable effects on ease and cost of production and characterization.

Example 12

PADRE Peptides Conjugated to Carbohydrates

This example describes the synthesis and use of a PADRE/carbohydrate conjugate to induce an antibody response.

a. Peptide Synthesis

The peptide aKXVAAWTLKAAaZC (X=L-Cyclohexylalanine, Z=Aminocaproic acid) was prepared according to standard solid phase peptide synthesis procedures, following an Fmoc synthesis strategy.

b. Carbohydrate Synthesis

Carbohydrate synthesis was carried out as shown in Scheme I, i. 1,2,3,6-Tetra-O-benzoyl-α-D-galactopyranoside (1).

A solution of galactose (10 g, 55.5 mmole) in 200 mL of pyridine was cooled to 0° C. under argon, benzoyl chloride (26.2 mL, 225 mmole) diluted in 10 mL of pyridine was added dropwise over 15 minutes. The mixture was stirred at 0° C. for 2 hours. Ice was then added to the solution, and the reaction mixture diluted with CH$_2$Cl$_2$ (500 mL) and washed with 20% H$_2$SO$_4$ (300 mL), saturated NaHCO$_3$ (300 mL), water (500 mL) and dried (Na$_2$SO$_4$). After filtration and concentration, the crude product was chromatographed (silica, 10% ethyl acetate/toluene) to yield 10.43 g (31%) of a white solid: R$_f$=0.3 (silica, 10% ethyl acetate/toluene). $^1$H-NMR (CDCl$_3$) δ 8.10 (d, 2 H, aromatic), 8.00 (t, 4 H, aromatic), 7.86 (d, 2 H, aromatic), 7.80–7.36 (m, 9 H, aromatic), 7.27 (t, 3 H, aromatic), 6.82 (d, J=3.7 Hz, 1 H, H-1), 6.07 (dd, J=3.7, 10.7 Hz, 1 H, H-2), 5.88 (dd, J=2.9, 10.7 Hz, 1 H, H-3), 4.78 (dd, J=6.3, 10.6 Hz, 1 H, H-6), 4.574.46 (m, 3 H).

ii. 1-Chloro-2,3,4,6-tetra-O-benzyl-α-D-galactopyranoside (2).

Oxalyl chloride (8.8 mL, 100 mmole) was added very slowly to a solution of 2,3,4,6-tetra-O-benzyl-D-galactopyranose (4.5 g, 8.2 mmole) in DMF (80 mL) at −20° C. under argon. The mixture was then allowed to warm to 0° C. and after 2 hours, 5 mL of additional oxalyl chloride was added. After an additional three hours, the reaction was diluted with $CH_2Cl_2$ (150 mL) and washed with ice water (200 mL), saturated $NaHCO_3$ (150 mL), water (150 mL) and dried ($Na_2SO_4$). Concentration afforded a crude product that was used without purification; $R_f$=0.8 (silica, 10% ethyl acetate/toluene).

iii. (2,3,4,6-tetra-O-benzyl-α-D-galactopyranosyl)-(1-4)-O-1,2,3,6-tetra-O-benzoyl-α-D galactopyranoside (3).

A suspension of 4 Å molecular sieve (400 mg), compound 1 (2 g, 3.35 mmole), collidine (1 mL, 7.37 mmole), AgOTf (2.58 g, 10 mmole) in 10 mL of toluene was cooled to −20° C. under argon. A solution of compound 2 in 10 mL of toluene was then added dropwise and stirred for 1 hour at −20° C. The reaction was allowed to warm to room temperature overnight, the suspension filtered through celite and the filtrate washed with 1N HCl (50 mL), water (50 mL), saturated $NaHCO_3$ (50 mL), water (50 mL) and dried ($Na_2SO_4$). Concentration and chromatography (silica, 2% to 10% ethylacetate/toluene) afforded 3.1 g (82%) of a white solid; $R_f$=0.7 (silica, 5% ethyl acetate/toluene). $^1$H-NMR ($CDCl_3$) δ 8.06 (d, 2 H, aromatic), 7.96 (m, 4 H, aromatic), 7.83 (dd, 2 H, aromatic), 7.62–7.11 (m, 32 H, aromatic), 6.84 (d, J=3.7 Hz, 1 H, H-1), 6.06 (dd, J=3.7, 11 Hz, 1 H, H-2), 5.77 (dd, J=2.6, 11 Hz, 1 H, H-3), 4.97 (d, J=3.4 Hz, 1 H, H-4), 4.89–4.06 (m, 14 H), 3.97 (s, 2 H, benzyl), 3.37 (dd, J=7.9, 7.9 Hz, 1 H), 2.88 (dd, 1H).

iv. (α-D-galactopyranosyl)-(1-4)-O-1,2,3,6-tetra-O-benzoyl-α-D-galactopyranoside (4).

Compound 3 (3.08 g, 2.75 mmole) was dissolved in 30 mL of acetic acid and degassed. Palladium on carbon (0.5 g, 10% by weight) was then added and the mixture was placed under a $H_2$ atmosphere (balloon) for 3 days. The solution was degassed, filtered through celite and concentrated. The residue was chromatographed (silica, 5% $CH_3OH/CH_2Cl_2$) to afford 1.48g (70%) of a white solid: $R_f$=0.35 (silica, 5% $CH_3OH/CH_2Cl_2$)-$^1$H-N ($CDCl_3$) d 8.09 (d 2 H, aromatic), 8.00–7.91 (m, 4 H, aromatic), 7.83 (d, 2 H, aromatic), 7.65–7.36 (m, 10 H, aromatic), 7.27 (d, 1H, aromatic), 7.25 (d, 1 H, aromatic), 6.82 (d, J=3.7 Hz, 1 H, H-1), 6.06 (dd, J=3.7, 10.9 Hz, 1 H, H-2), 5.81 (dd, J=2.6, 11 Hz, 1 H, H-3), 5.14 (d, J=2.9 Hz, 1 H, H-4), 4.77–4.61 (m, 3 H), 4.17–3.95 (m, 5 H), 3.38–3.18 (m, 2H).

v. (2,3,4,6-Tetra-O-benzoyl-α-D-galactopyranosyl)-(1-4)-O-1,2,3,6-tetra-O-benzoyl-α-D-galactopyranoside (5).

A solution of compound 4 (1.48 g, 1.95 mmole) in 20 mL of pyridine was cooled to 0° C. under argon and benzoyl chloride (1.81 mL, 15.6 mmole) was added dropwise and allowed to warm to room temperature overnight. The solution was then diluted with $CH_2Cl_2$ (100 mL), washed with 2M $H_2SO_4$ (100 mL), saturated $NaHCO_3$ (100 mL), water (100 mL) and dried ($Na_2SO_4$). Concentration and chromatography (silica, 5% ethyl acetate/toluene) afforded 2.03g (88%) of an oil; $R_f$=0.35 (silica, 5% ethyl acetate/toluene); $^1$H-NMR ($CDCl_3$) δ 8.12 (d, 2 H, aromatic), 8.08–7.94 (m, 5 H, aromatic), 7.88–7.79 (m, 7 H, aromatic), 7.63–7.12 (m, 26 H, aromatic), 6.88 (d, J=3.8 Hz, 1 H, H-1), 6.26–6.16 (m, 3 H, H-2, H-2', H-4'), 5.87 (dd, J=2,5, 11 Hz, 1 H, H-3), 5.85 (dd, J=3.4, 10.9 Hz, 1 H, H-3), 5.67 (d, J=3.6 Hz, 1 H, H-1'), 5.03 (dd, J=7.6 Hz, 1 H), 4.78 (d, J=2.6 HZ, 1 H, H-4), 4.64–4.55 (m, 2 H), 4.36–4.31 (m, 1 H), 4.04 (dd, J=8.4, 10.9 Hz, 1 H), 3.94 (dd, J=5.6, 11 Hz, 1 H).

vi. Bromo(2,3,4,6-Tetra-O-benzoyl-α-D-galactopyranosyl)-(1-4)-O-2,3,6-tri-O-benzoyl-α-D-galactopyranoside (6).

Hydrogen bromide (33%) in acetic acid (mL) was slowly poured into a solution of compound 5 (2.03 g 1.73 mmole) in acetic acid (mL) at 0° C. The solution was stirred at room temperature for 1 hour and was then diluted with $CH_2Cl_2$ (200 mL), washed with ice water (200 mL), saturated $NaHCO_3$ (200 mL) until neutral and dried ($Na_2SO_4$). Concentration afforded a pale yellow solid (1.84 g, 94%) that was used directly for the next step; $R_f$=0.4 (silica, 5% ethyl acetate/toluene).

vii. 2-Bromoethyl (2,3,4,6-Tetra-O-benzoyl-α-D-galactopyranosyl)-(14)-O-2,3,6-tri-O-benzoyl-β-D-galactopyranoside (7).

A solution of compound 6 (1.845 g, 1.63 mmole) dissolved in 10 mL of toluene was added dropwise to a mixture of 2-bromo ethanol (0.49 mL, 6.92 mmole), silver triflate (0.53 g, 2.076 mmole), collidine (114 μL 0.865 mmole) and toluene (15 mL) at 0° C. under argon. The suspension was allowed to warm to room temperature overnight and was washed with 2M $H_2SO_4$ (100 mL), saturated $NaHCO_3$ until neutral and dried ($Na_2SO_4$). Concentration and chromatography (silica, 3% ethyl acetate/toluene) afforded 1.38 g (72%) of a white solid; $R_f$=0.3 (silica, 5% ethyl acetate/toluene). $^1$H-NM ($CDCl_3$) δ 7.98–7.78 (m, 16 H, aromatic), 7.59–7.20 (m, 19 H, aromatic), 6.21 (dd, J=3.3, 10.8 Hz, 1 H, H-2'), 6.14 (bd, 1 H, H-4'), 5.88 (dd, J=7.7, 10.5 Hz, 1 H, H-2), 5.79 (dd, J=3.6, 10.9 Hz, 1 H, H-3'), 5.61 (d, J=4.4 Hz, 1 H, H-1'), 5.34 (dd, J=2.8, 10.6 Hz, 1 H, H-3), 4.98 (bt, 1 H), 4.85 (d, J=7.6Hz, 1 H, H-1), 4.70 (dd, J=6.5, 11.2 Hz, 1 H), 4.57 (d, J=2.6 Hz, 1 H, H-4), 4.36 (dd, J=7.5, 11.2 Hz, 1 H), 4.18–4.00 (m, 4 H), 3.93–3.05 (m, 1 H), 3.46–3.39 (m, 2 H).

viii. 2-Bromoethyl(α-D-galactopyranosyl)-(1-4)-O-β-D-galactopyranoside (8).

Sodium methoxide in methanol (25% by weight, 2 mL) was added dropwise to a solution of compound 7 (1.38 g, 1.18 mmole) in 100 mL of methanol. The mixture was stirred under argon for two days, neutralized with AG 50WX8 ($H^+$) resin, filtered and concentrated. The residue was chromatographed (C-18 silica, water to 5% $CH_3OH$/water) to afford 570 mg (100%) of a white solid; $R_f$=0.1 (silica, $CH_2Cl_2/CH_3OH$/water (80/20/1)). $^1$H-NMR ($D_2O$) d 4.95 (d, J=3.8 Hz, 1 H, H-1'), 4.52 (d, J=7.1 Hz, 1 H, H-1), 4.37 (dd, J=6.6, 6.6 Hz, 1 H), 4.25–4.17 (m, 1 H), 4.07–4.00 (m, 3 H), 3.93–3.54 (m, 18 H; MS (FAB+) m/z 471 ($M^+$+$Na^+$), 473 ($M(^{81}Br^+$+$Na^+$).

c. Reaction of 2-Bromoethyl (α-D-galactopyranosyl)-(1-4)-O-β-D-galactopyranoside (8) with the polypeptide aKX-VAAWTLKAAaZC.

The peptide was conjugated to the 2-Bromoethyl (α-D-galactopyranosyl)-(1-4)-O-β-D-galactopyranoside by reaction of the sulfhydryl group of the cysteine residue with the bromoethyl group of the glycoside. The peptide residues, aminocaproic acid, and cysteine, together with the ethylene moiety of the glycoside, form a spacer between the disaccharide Gal-Gal and the peptide sequence aKXVAAWTL-KAAa.

In a typical procedure 1.27 μmoles of peptide, 2.55 μmoles of bromethyl glycoside and 25 μmoles of $CS_2CO_3$ were added to 1 mL of carefully degassed, dry dimethylformamide and maintained under an argon atmosphere for the duration of the reaction. The mixture was sonicated for 5 minutes and then stirred at room temperature for 2 hours. The dimethylformamide was evaporated in vacuo. The residue was dissolved in 2 mL of 20% aqueous acetic acid and purified by preparative high performance liquid chromatography.

d. Immunizations

C57BL/6J ($H-2^b$) mice, 8 to 16 weeks old, were injected at the base of the tail with 70 μg/mouse of PADRE-sugar in 100 μl of complete Freund's adjuvant (CFA) (Difco Lab, Detroit, Mich.) and bled 4 weeks later. They were subsequently boosted with the same amount of peptide-sugar compound in 100 μl of incomplete Freund's adjuvant (IFA) and bled again 2 weeks later. Antibody titers (primary and secondary response) were measured using an ELISA assay.

e. Elisa

100 μL of carboxyethylthioethyl 4-O-α-OGalactopyranosyl-β-O-Galactopyranoside-BSA (Sigma, St. Louis, Mo.) conjugated in PBS (10 μg/mL) was added to each well of a 96-well flat bottom plate (Immunol II, Dynatech). After blocking with 0.1% BSA, 0.05% Tween 20 in PBS, serial dilutions of the sera from immunized mice were added and the plates incubated 1 hour at 37° C. The plates were washed with PBS +0.05% Tween-20 then incubated for 2 hours at room temperature with Biotin Conjugated Goat affinity purified antibody to mouse (whole molecule) IgG (Cappel, Durham, N.C.), and IgM (Caltag Lab, San Francisco, Calif.). The washed plates were then incubated with a complex Avidin DH and biotinylated horseradish peroxidase H (Vectastain ABC Kit, Vector Lab, Burlingame, Calif.). The bound anti-sugar antibody was detected with the TMB Peroxidase substrate (Kirkegaard and Perry Laboratories, Gaithersberg, Md.). All measurements were performed in duplicate and the antibody titers were defined as the serum dilution yielding 0.3 O.D. units.

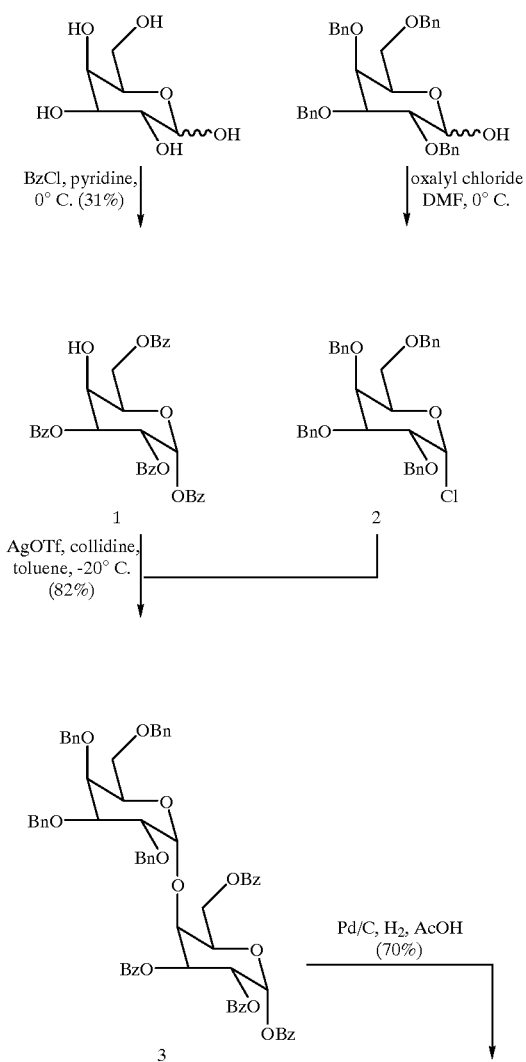

Scheme I

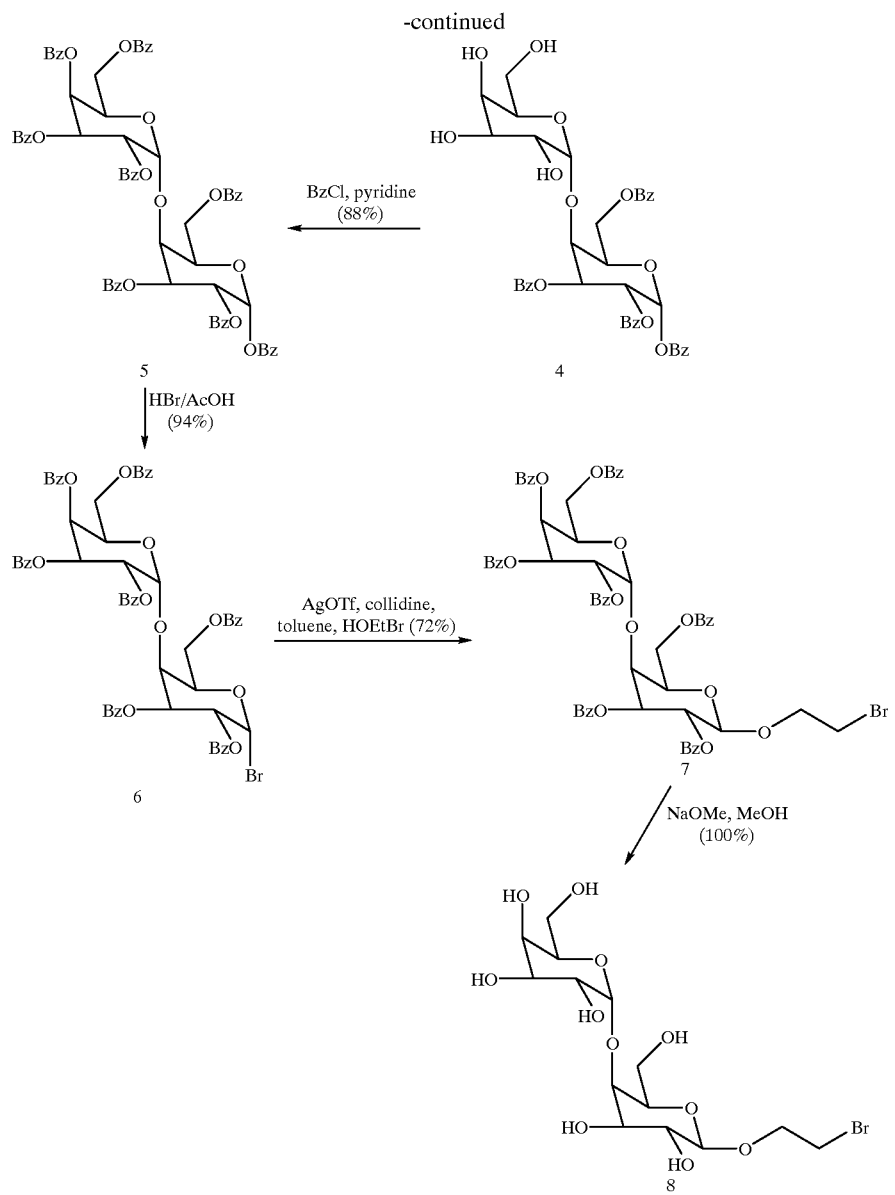

e. Results

The results obtained (Table VII) show that C57B1/6J mice responded very well to the disaccharide Gal-Gal. After a single injection, the humoral response was predominately IgG with a mean titer of approximately $4.3 \times 10^4$.

TABLE VII

Antibody response to PADRE-sugar 1-10-96

| IMMUNOGEN | ISOTYPES | 1 month after 1st immunization |
|---|---|---|
| CFA | IgG | 127*/2.24 |
|  | IgM | 77*/1.05 |
| PADRE-sugar | IgG | 42654*/2.69 |
|  | IgM | 100*/11.5 |

Example 13

Antibody Responses to Penta- and Dodecasaccharides

Figures 5A, 5B, 5C:
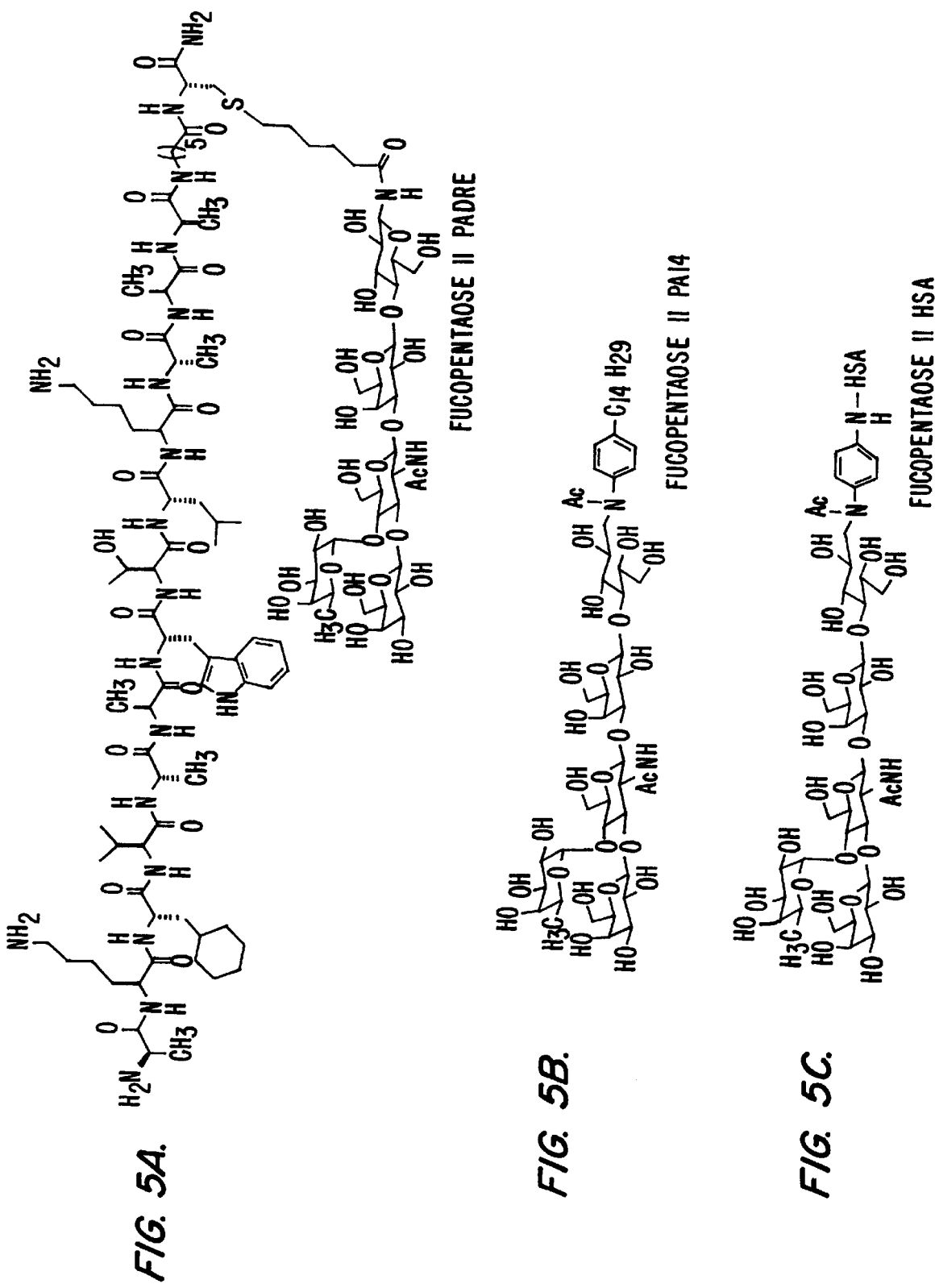
FIGS. 5A, B and C indicate the structures of the pentasaccharide fucopentaose II and its conjugates; (A) fucopentaose II-PADRE, (B) fucopentaose II-PA14, and (C) fucopentaose II-HSA.
Figure 6A:
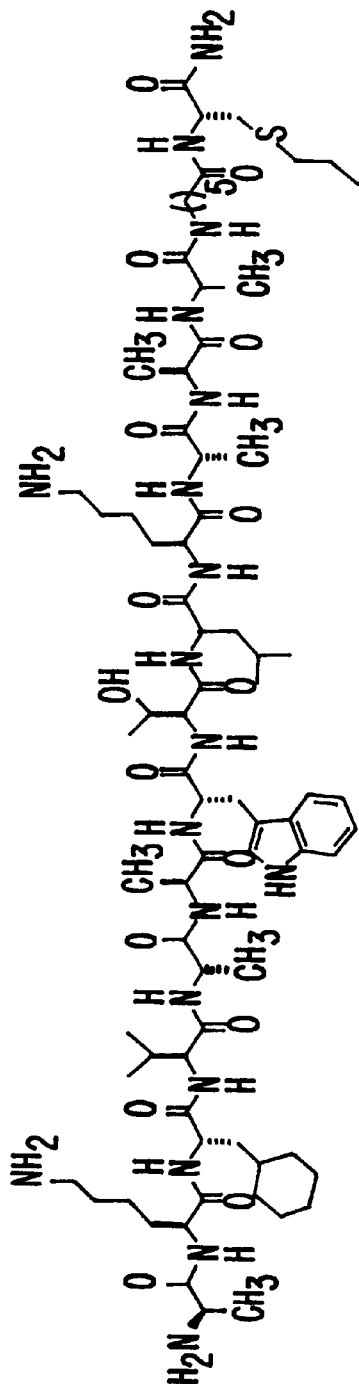
FIGS. 6A and B represent the structures of (A) dodecasaccharide-PADRE conjugate and (B) *Salmonella typhimurium* LPS.
Figure 6B:
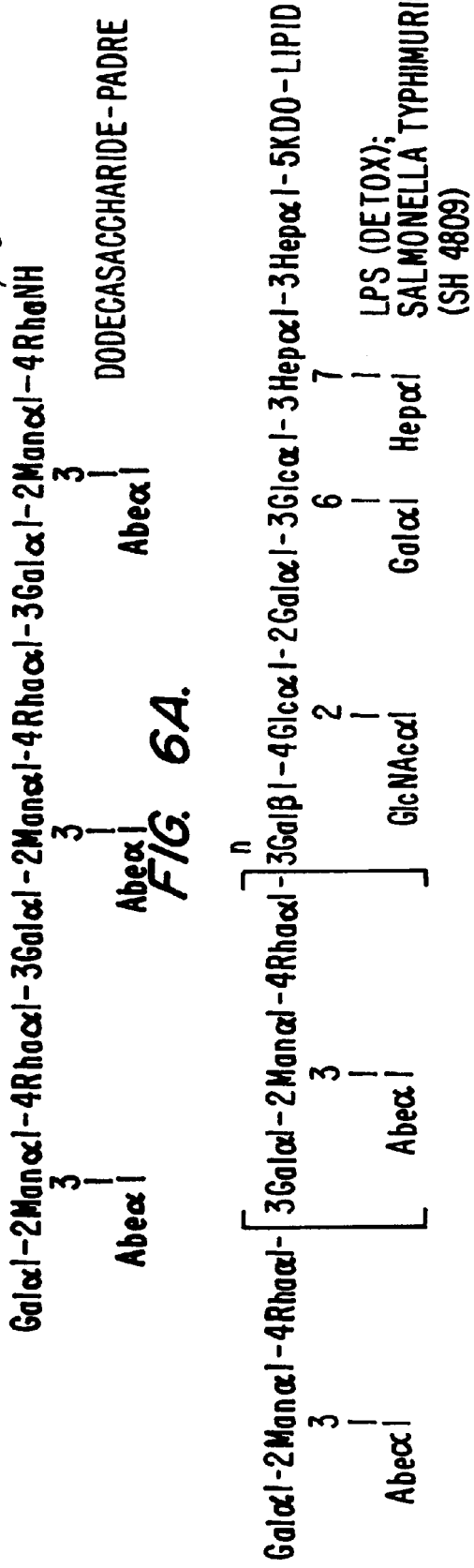

The structures of the saccharides, the saccharide-PADRE conjugates and the immunization controls are given in FIGS. 5A, B and C; and 6A and B.

a. Carbohydrate Synthesis i. N-6-bromocaproyl β-D-Galactopyranosyl-(1→3)-[α-L-Fucopyrannosyl](1→4)-β-D-2-N-acetimidoglucopyranosyl-(1→3)-β-D-Galactopyranosyl-(1→4)-β-D-glucopyranosylamine (Bromocaproyl Lacto-N-fucopentaose II) (9)

A solution of lacto-N-fucopentaose II (10.0 mg, 11.7 μmol) in saturated $NH_4HCO_3$ (5 mL) was stirred at room temperature for 3 days with solid $NH_4HCO_3$ added in fractions during this time to ensure saturation. The mixture was repeatedly lyophilized until a consistent weight was obtained. This yielded a white fluffy solid used directly in the next step without further purification.

The resulting solid was suspended in THF (2.0 mL) and cooled to 4° C. Saturated NaHCO$_3$ (2.0 mL) was then added to the solution followed by 6-bromocaproyl chloride (20 μL, 131 μmol). After 10 min., an additional portion of 6-bromocaproyl chloride (20 μL, 131 μmol) was added and the stirring was continued at 0° C. for 2 hours, and then room temperature for 2 hours. Water (5 mL) was then added to the reaction mixture and the solution was acidified to pH 5 by addition of 1.0 M HCl. After extraction of the reaction mixture with diethyl ether (5 mL×3), the aqueous phase was concentrated to approximately 2 mL and chromatographed (C-18 silica gel, 0% methanol in H$_2$O to 20% methanol in H$_2$O). After concentration and lyophilization, a white solid (6.5 mg, 53% yield) was obtained.

$^1$H NMR (D$_2$O; 300 MHZ) δ 1.96 (d, 1 H, J=1.0 Hz), 4.92–4.6 (m), 4.45 (d, 1 H, J=7.1 Hz), 4.4 (d, J=7.1 Hz), 4.1 3.35 (m, 30 H), 2.3 (t, 1 H, J=7.0 Hz) 2.1 (t, 1 H, J=7.0 Hz), 1.9 (s, 3 H), 1.8–1.72 (m, 2 H), 1.60–1.50 (m, 2 H), 1.45–1.32 (m, 2 H), 1.1 (t, J=7.0 Hz, 3 H).

ii. N-6-Bromocaproyl α-D-Galactopyranosyl-(1→2)-[α-L-abequosyl](1→3)-α-D-mannopyranosyl-(1→4)-α-D-rhamnosyl-(1→3)-α-D-galactopyranosyl-(1→2)-[α-L-abequosyl](1→3)-α-D-mannopyranosyl-(1→4)-α-D-rhamnosyl-(1→3)-α-D-galactopyranosyl-(1→2)_[α-L-abequosyl](1→3)-α-D-mannopyranosyl-(1→4)-α-D-rhamnosylamine (Bromocaproyl Dodecasaccharide) (10)

A solution of dodecasaccharide (6.0 mg, 3.29 μmol) in saturated NH$_4$CO$_3$ (1.5 mL) was stirred at room temperature for 4 days with solid NH$_4$HCO$_3$ added in fractions during this time to ensure saturation. Repeated lyophilization of the reaction mixture until a consistent weight afforded a white fluffy solid used directly in the next step without further purification.

The resulting solid was suspended in THF (0.5 mL) and cooled to 0° C. Saturated NaHCO$_3$ (0.5mL) was then added to the solution followed by 6-bromocaproyl chloride (2 μL, 13.1 μmol). After 10 min., an additional portion of 6-bromocaproyl chloride (8 μL, 542 μmol) was added and the stirring was continued at 0° C. After a further 2 hours, a further portion of the 6-bromocaproyl chloride (8 μL) was added and the reaction mixture was stirred at 0° C. for 2 hours, and room temperature for 2 hours. The reaction mixture was then diluted with water (5 mL) and acidified to pH 5 by addition of 1.0 M HCl. This solution was extracted with diethyl ether and the separated aqueous phase was concentrated to about 2 mL and chromatographed (C-18 reverse silica gel, 0% methanol in H$_2$O to 20% methanol in H$_2$O). After concentration and lyophilization a white solid was obtained (3.28 mg, 50% yield). $^1$H NMR (D$_2$O), 300 MHZ) δ 5.25 (s), 5.08 (d, 1 H, J=3.3 Hz), 5.00 (d, 1 H, J=3.6 Hz), 1.97 (s, 1), 4.85 (d, 1 H, J=2.2 Hz), 4.05–3.30 (m), 2.25 (t, 1 H, J=7.0 Hz), 210 (t, 1 H, J=7.3 Hz), 1.90 (br, d, 3 H, J=8.8 Hz), 1.82–1.74 (m, 2 H), 1.60–1.45 (m, 2 H) 1.4–1.3 (m, 2 H), 1.21 (d, 3 H, J=6.0 Hz), 1.10–1.02 (m, 6 H); MS (Electrospray) m/z Calcd for C$_{78}$H$_{132}$ BrNO$_{52}$: 1995. Found: 1993, 1995.

b. Saccharide-Padre Conjugation i. Lacto-N fucopentaose II-PADRE Conjugate (Pentasaccharide-PADRE)

A mixture of the bromocaproyl lacto-N-fucopentaose (2.3 mg, 2.2 μmol), PADRE peptide (3.1 mg, 2.2 μmol), and cesium carbonate (14 mg, 44 μmol) in anhydrous DMF (1.0 mL, degassed with argon before use) was stirred at room temperature under an argon atmosphere for 24 hours. The reaction mixture was concentrated in vacuo and the resulting solid was dissolved in water (0.5 mL). Purification by HPLC (Vydac C-18 column, 25% CH$_3$CN, 75% H$_2$O to 35% CH$_3$CN, 65% H$_2$O in 55 min, flow rate of 2.0 mL/min) gave the lacto-N-fucopentaose II-PADRE conjugate (2.5 mg, 45% yield).

$^1$H NMR (D$_2$O; 300 MHZ) δ 1.96 (d, 1 H, J=4.0 Hz), 4.92–4.6 (m), 4.45 (d, 1 H, J=7.1 Hz), 4,4 (d, J=7.1 Hz), 4.1 3.35 (m, 30 H), 2.3 (t, 1 H, J=7.0Hz), 2.1 (t, 1 H, J=7.0 Hz), 1.9 (s, 3 H), 1.8–1.72 (m, 2 H), 1.60–1.50 (m, 2 H), 1.45–1.32 (m, 2 H), 1.1 (t, J=7.0 Hz, 3 H).

ii Dodecasaccharide-PADRE Conjugate

A mixture of the bromocaproyldodecasaccharide (1.61 μmol), the PADRE peptide (3.8 mg, 2.46 μmol), and cesium carbonate (10.7 mg, 33 μmol) in anhydrous DMF (1.0 mL, degassed with argon before use) was stirred at room temperature under an argon atmosphere for 14 hours. The reaction mixture was concentrated in vacuo. The resulting solid was dissolved in H$_2$O (1.8 mL), DMSO (0.2 mL) and acetic acid (0.1 mL) and purified by HPLC (Vydac C-18 column, 25% CH$_3$CN, 75% H$_2$O to 42% CH$_3$CN, 58% H$_2$O in 55 min, flow rate of 2.0 mL/min). After concentration and lyophilization, a white solid (3.1 mg, 54% yield) was obtained.

$^1$H NMR (DMSO-d6; 500 MHZ) δ 8.52 (d, 1 H, J=8.07 Hz), 8.18 (d, 1 H, J=7.67 Hz), 8.10–7.61 (m), 7.75 (d, J=7.86 Hz), 7.46 (s. 1 H), 7.31 (d, 1 H, J=8.03 Hz), 7.2–7.5 (m), 7.04 (t, 1 H, J=7.32 Hz), 6.94 (t, 1 H, J=7.32 Hz), 5.01–0.80 (m): MS (Electropsray) m/z Calcd for C$_{152}$H$_{255}$N$_{19}$O$_{69}$S: 3482 found: 3483 (Mavg), 3505 (M$^+$Na$^+$), 3521 (M+K$^+$).

c. Immunizations

Three C57BL/6J (H-2$^b$) mice, 8 to 16 weeks old were injected at the base of the tail with 100 μg/mouse of immunogens in 100 μL of CFA and bled 4 weeks later. The mice were subsequently boosted with the same amount of immunogens in 100 μL of IFA and bled again 2 weeks later. The IgG and IgM titers were measured by an ELISA assay.

d. Elisa

1μg/well of lacto-N-fucopentaose II-HSA (Biocarb Cat. No. 61–03 (1990)) was added to each well of a 96-well flat bottom plate (Immunol II, Dynatech). After blocking with 0.1% BSA, 0.05% Tween 20 in PBS, serial dilutions of the sera from immunized mice were added and the plates incubated 1 hour at 37° C. The plates were washed with PBS +0.05% Tween-20 then incubated for 1 hour at room temperature with horse radish peroxidase (HRP)-rat antimouse IgG and an HRP-goat anti-mouse IgM. The bound anti-sugar antibodies was detected with the TMB Peroxidase substrate (Kirkegaard and Perry Laboratories, Gaithersberg, Md.). All measurements were performed in duplicate and the antibody titers were defined as the serum dilution yielding 0.3 O.D. units. Antibody responses directed to pentasaccharide immunogens are shown in Table X.

Antibody responses directed to dodecasaccharide immunogens are shown in Table XI. In this ELISA, the wells were coated with 10 μg/mL of LPS. The ELISA reagents used were the same as with the pentasaccharide ELISA. Titers were defined as the serum dilution yielding 0.3 O.D. units.

TABLE X

Antibody responses to pentasaccharide (12/17/96)

| IMMUNOGENS | Isotypes | Antibody titers 1 month after 1$^{st}$ immunization | Boost |
| --- | --- | --- | --- |
| CFA | IgG | 0 | 0 |
|  | IgM | 38 | 56 |
| Lacto-N- | IgG | 0 | 0 |

TABLE X-continued

Antibody responses to pentasaccharide (12/17/96)

| IMMUNOGENS | Isotypes | Antibody titers 1 month after 1st immunization | Boost |
|---|---|---|---|
| Fucopentaose II-PA14 | IgM | 37 | 50 |
| PADRE-pentaose II | IgG | 3632 | 27968 |
|  | IgM | 200 | 198 |

TABLE XI

Antibody responses to dodecasaccharide (12/17/96)

| IMMUNOGENS | Isotypes | Antibody titers 1 month after 1st immunization | Boost |
|---|---|---|---|
| CFA | IgG | 0 | 49 |
|  | IgM | 528 | 94 |
| LPS | IgG | 53 | 882 |
|  | IgM | 68 | 724 |
| PADRE-dodecasaccharide | IgG | 7109 | 87435 |
|  | IgM | 1284 | 698 | e. Discussion

The experiments presented herein demonstrate that PADRE peptides can be utilized to raise powerful antibody responses to carbohydrate moieties. When conjugated to pentasaccharides, there is a large increase in the IgG response 1 month after immunization when compared to pentasaccharide alone. And after a boosting injection, the antibody titer shows an even greater increase. Also of importance is the increased IgG response compared to IgM. IgG responses are of a longer term and typically IgG antibodies are of greater affinity.

Similar results are seen with dodecasaccharide PADRE conjugates. There remains a large increase in IgG response when LPS-derived polysaccharide is conjugated to PADRE compared to immunizations with LPS alone. Again, the strength of the IgG response is important in that the response is of a longer term and typically, IgG antibodies are of higher affinity than IgM antibodies.

In conclusion, the experiments presented herein demonstrate that PADRE peptides can be utilized to raise powerful antibody responses to a carbohydrate moiety. Because of their very broad spectrum of reactivity, it is anticipated that use of PADRE peptides should allow for coverage of a very high fraction of the human population, higher than the one covered by either "universal" T cell epitopes, such as TT 830–843 and others (see Alexander, et al. op. cit.). The use of PADRE peptides could simplify constructs, with favorable effects on ease and cost of production and characterization. We anticipate that PADRE peptides conjugated to various carbohydrate moieties (sources may include viral, bacterial, fungal tumor, or parasitic) may be developed for diagnostic, prophylactic, or therapeutic disease applications.

Example 14

Use of Analogs of Known DR Binders to Generate Peptides with Broad Class H Binding Capacity An alternative approach to generate peptides with broad specificity and high affinity for MHC class II molecules entails using known DR binding peptides and introducing various amino acid changes at positions other than those previously identified as crucial MHC motif residues. Each of these analogs is then tested for class II binding in molecular binding assays as described in the previous examples.

In the set of experiments described herein the peptide 760.57 (aAXAAAATLKAAa) was selected as a starting point for further modification. Peptide 760.57, while not binding appreciably to alleles DR3, DR52a, and DRw53 does however bind well to DR1, 2, 4, 5, and 7. In order not to interfere with the binding capacity to these alleles no substitutions were introduced for the aromatic residue in position 3, for the threonine residue in position 8 and for the alanine residue in position 11. The D-amino acids included at the N- and C-termini to reduce sensitivity to proteolytic degradation (Lamount, et al., *J. Immunol.* 144:2493 (1990)) were also left unmodified. Four to six amino acid changes were incorporated at other positions (2, 5, 6, 7, 9, 10, and 12) thus generating other 906 series analogs.

Generally, the amino acid substitutions included a positively (K) and negatively (E) charged amino acid, a hydrophilic amino acid (Q), one aliphatic amino acid (V and/or L and/or I), and the aromatic amino acid (F). The binding data obtained when these peptides were tested for binding to a panel of human class II molecules is shown in Table VIII. In general, since the positions crucial for DR1, 2, 4, 5, and 7 binding (positions 3, 8, and 11) had not been modified, good binding capacity was retained. Unless otherwise indicated binding capacity for these alleles was not altered by more than 5 fold. For ease of discussion, in this example, positions are referred to as 1 to 13 from N to C:

a. Position 2[A]:

The hydrophilic Q (906.03) or the aliphatic V (906.04) substitution induced impressive 30 to 100 fold increases in DR53 reactivity. More modest increases (3-fold) in DR3 reactivity were also induced by the same substitutions. In addition, an approximate 10 fold increase in DQ3.1 binding reactivity was observed for all substitutions tested at this position. Finally, some DR52a reactivity was gained by analogs K (906.01), and Q (906.03).

b. Position 5[A]:

A modest increase of 2 to 4-fold DR3 binding was accomplished with a V (906.16) or F (906.17). Again impressive (≈100-fold) increases were also demonstrated with the same analogs 906.16 and 906.17 for DR53 reactivity. A modest loss (7 fold) of DR1 binding reactivity was observed for a E (906.14) modification. Most modifications at this position resulted (with the exception of F (906.17)) in significant losses of DQ3.1 binding capacity.

c. Position 6[A]:

A reasonable DR3 reactivity (IC50≈1500 nM) and some reactivity for DR52a binding were demonstrated with the negatively charged amino acid substitution, E (906.19). An impressive increase in DR53 reactivity (20 fold) was also seen with the same 906.19 analog. However, DR7 reactivity was lost. The K modification (906.18) decreased binding activity of DR1 (8-fold), DR4w14 (10-fold) and DR7 (no detectable binding). The hydrophilic modification Q, (906.20) resulted in loss of DR3 binding and DR7 binding was reduced by 30-fold. Finally, decreases in DQ3.1 binding capacity were also seen with all substitutions tested at this position.

d. Position 7[A]; 9[L]; and 10[K]:

The only appreciable binding reactivity gained (≈10 fold) with substitutions made at these positions was for DQ3.1. The exceptions being 906.29 (K at position-9) and 906.30 (E at position 9) where no reactivity was gained. It is also interesting to note that the analog 906.30 demonstrated a loss of binding reactivities for DR1 (8-fold), DR4w4 (7-fold) DR4w14 (8-fold), DR5 (10-fold), and DR7 (10- fold). Also, it was noted for position 9 that DR3 reactivity was lost for 4 out of 6 substitutions.

e. Position 12[A]:

Peptide analog 906.50 with an aromatic F substitution increased DR3 and DRw53 reactivities by 8 and 40-fold, respectively. In addition, DR52a binding reactivity was gained with the F substitution.

Second generation (906.51, 906.52, 906.53, 906.55, and 906.56) analogs were also synthesized using combinations of substitutions that in the set of experiments described above, increased DR3 and/or DR52a reactivities (906.04 (V) at position 2; 906.09 (V) at position 4; 906.16 (V) or 906.17 (F) at position 5; and 906.50 (F) at position 12). In general, these second generation analogs also demonstrated good reactivity for most of the DR alleles tested (with the exception of the 906.55 analog binding to DR52a).

In the next series, 965.01 to 965.19, analogs of 906.09 were generated by introducing bulky or charged amino acids at non-critical MHC contact residues. In general, high- or intermediate-capacity binding was maintained (Table IX) for DR1, 2w2β2, 4w4, 4w14, 5, 7 and DRw53. Binding capacity varied for DR3.

TABLE VIII A

PADRE Class II Binding Affinities

| PEPTIDE | LEN | SEQUENCE | SOURCE | DR1 nM | DR2w261 nM | DR2w282 nM | DR3 nM | DR4w4 nM | DR4w14 nM | DR5 nM | DR7 nM | DR52a nM | DRw53 nM | DOG.1 nM |
|---|---|---|---|---|---|---|---|---|---|---|---|---|---|---|
| 906.01 | 13 | aK(14)AAAATLKAAa-NH2 | 760.57 SAAS | 1.70 | | 2.7 | 3782 | 1.9 | 5.0 | 4.9 | 83.3 | 5663 | | 25.3 |
| 906.02 | 13 | aE(14)AAAATLKAAa-NH2 | 760.57 SAAS | 3.60 | | 4.5 | 2406 | 3.0 | 11.4 | 5.4 | 168.7 | 18077 | | 29.9 |
| 906.03 | 13 | aO(14)AAAATLKAAa-NH2 | 760.57 SAAS | 1.70 | 41.94 | 1.8 | 1480 | 2.4 | 2.1 | 3.7 | 53.2 | 5341 | 35.3 | 16.3 |
| 906.03 | 13 | aQ(14)AAAATLKAAa-NH2 | 760.57 SAAS | 1.20 | | 3.7 | 9184 | 2.9 | 2.5 | 3.3 | 100.0 | 4700000 | | 12.3 |
| 906.04 | 13 | aV(14)AAAATLKAAa-NH2 | 760.57 SAAS | 0.50 | 121.33 | 2.2 | 1654 | 2.6 | 3.7 | 3.0 | 125.0 | 11750 | 10.7 | 38.2 |
| 906.05 | 13 | aF(14)AAAATLKAAa-NH2 | 760.57 SAAS | 0.90 | | 1.8 | 2727 | 1.7 | 2.4 | 3.0 | 49.0 | 4608 | | 23.7 |
| 906.06 | 13 | aA(14)KAAATLKAAa-NH2 | 760.57 SAAS | 0.40 | | 3.8 | 2980 | 2.2 | 5.1 | 3.4 | 52.1 | 2009 | | 34.6 |
| 906.07 | 13 | aA(14)EAAATLKAAa-NH2 | 760.57 SAAS | 2.90 | | 16.6 | 6818 | 2.4 | 3.7 | 2.8 | 227.3 | 11190 | | 65.5 |
| 906.08 | 13 | aA(14)QAAATLKAAa-NH2 | 760.57 SAAS | 1.70 | | 3.1 | 3041 | 2.4 | 4.3 | 4.3 | 166.7 | 1114 | | 53.0 |
| 906.09 | 13 | aA(14)VAAATLKAAa-NH2 | 760.57 SAAS | 0.60 | 14.29 | 1.9 | 504 | 6.7 | 5.4 | 5.4 | 75.6 | 589 | 31.6 | 49.0 |
| 906.10 | 13 | aA(14)FAAATLKAAa-NH2 | 760.57 SAAS | 1.30 | | 4.0 | 3913 | 2.7 | 2.4 | 2.5 | 32.9 | 3267 | | 87.7 |
| 906.11 | 13 | aA(14)AAATLKAAa-NH2 | 760.57 SAAS | 0.40 | 19.00 | 1.3 | 180 | 4.5 | 3.4 | 4.8 | 30.5 | 1127 | 42.9 | 112.8 |
| 906.12 | 13 | aA(14)LAAATLKAAa-NH2 | 760.57 SAAS | 0.30 | 44.61 | 1.5 | 1293 | 2.9 | 3.4 | 2.4 | 44.6 | 1042 | 42.9 | 57.0 |
| 906.13 | 13 | aA(14)AKAATLKAAa-NH2 | 760.57 SAAS | 2.40 | 606.67 | 3.2 | 2848 | 3.7 | 4.6 | 4.8 | 92.5 | 94000 | 545.5 | 15000.0 |
| 906.14 | 13 | aA(14)AEAATLKAAa-NH2 | 760.57 SAAS | 6.10 | | 33.3 | 15517 | 4.2 | 13.9 | 2.9 | 328.9 | 42727 | | 2142.0 |
| 906.15 | 13 | aA(14)AQAATLKAAa-NH2 | 760.57 SAAS | 2.60 | | 1.7 | 7258 | 4.0 | 8.5 | 14.3 | 100.0 | 58750 | | 346.6 |
| 906.16 | 13 | aA(14)AVAATLKAAa-NH2 | 760.57 SAAS | 0.90 | 75.83 | 1.1 | 1098 | 5.2 | 5.7 | 5.7 | 108.7 | 8103 | 7.3 | 2142.9 |
| 906.17 | 13 | aA(14)AFAATLKAAa-NH2 | 760.57 SAAS | 1.50 | 14.80 | 1.0 | 2206 | 5.0 | 4.5 | 6.9 | 33.8 | 7460 | 18.2 | 76.5 |
| 906.18 | 13 | aA(14)AAKATLKAAa-NH2 | 760.57 SAAS | 6.80 | | 3.5 | 4500000 | 3.5 | 29.4 | 3.0 | 25000.0 | 4700000 | | 346.6 |
| 906.19 | 13 | aA(14)AAEATLKAAa-NH2 | 760.57 SAAS | 3.30 | 4550.00 | 9.5 | 1779 | 4.5 | 4.2 | 2.2 | 250000.0 | 1451 | 50.0 | 681.6 |
| 906.20 | 13 | aA(14)AAQATLKAAa-NH2 | 760.57 SAAS | 1.00 | | 3.3 | 56250 | 1.8 | 2.8 | 6.5 | 2500.0 | 470000 | | 652.2 |
| 906.21 | 13 | aA(14)AAVATLKAAa-NH2 | 760.57 SAAS | 0.20 | | 1.5 | 21429 | 3.0 | 4.1 | 4.1 | 42.4 | 13824 | | 426.6 |
| 906.22 | 13 | aA(14)AAFATLKAAa-NH2 | 760.57 SAAS | 1.70 | | 3.3 | 50000 | 2.4 | 2.8 | 3.2 | 59.4 | 13429 | | 1875.0 |
| 906.23 | 13 | aA(14)AAAKTLKAAa-NH2 | 760.57 SAAS | 0.70 | | 1.5 | 3333 | 2.0 | 5.5 | 3.4 | 29.6 | 20435 | | 26.1 |
| 906.24 | 13 | aA(14)AAAETLKAAa-NH2 | 760.57 SAAS | 2.10 | | 6.0 | 4891 | 2.6 | 4.5 | 2.2 | 373.1 | 1253 | | 46.6 |
| 906.25 | 13 | aA(14)AAAQTLKAAa-NH2 | 760.57 SAAS | 1.60 | | 1.7 | 2830 | 2.3 | 4.5 | 11.1 | 156.3 | 21364 | | 42.5 |
| 906.26 | 13 | aA(14)AAAVTLKAAa-NH2 | 760.57 SAAS | 1.00 | | 1.4 | 3191 | 2.2 | 3.9 | 3.0 | 65.8 | 979 | | 27.9 |
| 906.27 | 13 | aA(14)AAAFTLKAAa-NH2 | 760.57 SAAS | 0.50 | | 3.4 | 6061 | 2.2 | 1.7 | 3.9 | 65.8 | 23500 | | 44.1 |
| 906.28 | 13 | aA(14)AAATTLKAAa-NH2 | 760.57 SAAS | 1.80 | | 1.3 | 4839 | 4.5 | 7.4 | 2.6 | 69.4 | 10217 | | 28.5 |
| 906.29 | 13 | aA(14)AAAATKKAAa-NH2 | 760.57 SAAS | 2.80 | | 2.9 | 4500000 | 4.6 | 38.5 | 5.0 | 290.7 | 470000 | | 283.0 |
| 906.30 | 13 | aA(14)AAAATEKAAa-NH2 | 760.57 SAAS | 6.90 | | 25.9 | 30000 | 14.5 | 26.3 | 7.7 | 757.6 | 3219 | | 148.5 |
| 906.31 | 13 | aA(14)AAAATQKAAa-NH2 | 760.57 SAAS | 0.50 | | 1.9 | 18000 | 4.2 | 12.2 | 51.5 | 100.0 | 6528 | | 52.6 |

TABLE VIII A-continued

PADRE Class II Binding Affinities

| PEPTIDE | LEN | SEQUENCE | SOURCE | DR1 nM | DR2w261 nM | DR2w282 nM | DR3 nM | DR4w4 nM | DR4w14 nM | DR5 nM | DR7 nM | DR52a nM | DRw53 nM | DOG.1 nM |
|---|---|---|---|---|---|---|---|---|---|---|---|---|---|---|
| 906.32 | 13 | aA(14)AAAAITVKAAa-NH2 | 760.57 SAAS | 0.40 | | 2.6 | 18750 | 3.3 | 3.1 | 4.2 | 58.1 | 5402 | | 26.0 |
| 906.33 | 13 | aA(14)AAAAITFKAAa-NH2 | 760.57 SAAS | 0.70 | | 1.7 | 11538 | 1.5 | 3.0 | 2.4 | 43.1 | 22381 | | 13.4 |
| 906.34 | 13 | aA(14)AAAAITIKAAa-NH2 | 760.57 SAAS | 0.50 | | 2.3 | 6818 | 2.3 | 3.0 | 3.1 | 55.6 | 4017 | | 30.5 |
| 906.35 | 13 | aA(14)AAAAITLEAAa-NH2 | 760.57 SAAS | 1.70 | | 15.3 | 11538 | 3.7 | 3.9 | 10.5 | 168.7 | 9400 | | 39.5 |
| 906.36 | 13 | aA(14)AAAAITLQAAa-NH2 | 760.57 SAAS | 2.30 | | 3.5 | 4945 | 2.8 | 3.7 | 8.3 | 119.0 | 24737 | | 23.7 |
| 906.37 | 13 | aA(14)AAAAITLVAAa-NH2 | 760.57 SAAS | | | | | | | | | | | |
| 906.38 | 13 | aA(14)AAAAITLFAAa-NH2 | 760.57 SAAS | 2.60 | | 3.9 | 4500000 | 2.7 | 6.8 | 19.2 | 56.8 | 12051 | | 14.3 |
| 906.39 | 13 | aA(14)AAAAITLRAAa-NH2 | 760.57 SAAS | 1.10 | | 1.0 | 3846 | 3.5 | 2.9 | 4.3 | 86.2 | 24737 | | 28.8 |
| 906.40 | 13 | aA(14)AAAAITLKKa-HH2 | 760.57 SAAS | 71.40 | 4550.00 | 0.5 | 1931 | 11.0 | 29.4 | 16.7 | 555.6 | 4700000 | 2307.7 | 36.6 |
| 906.41 | 13 | aA(14)AAAAITLKEAa-NH2 | 760.57 SAAS | 238.10 | | 28.5 | 20455 | 8.8 | 228.3 | 285.7 | 252.5 | 470000 | | 227.3 |
| 906.42 | 13 | aA(14)AAAAITLKQa-NN2 | 760.57 SAAS | 11.60 | | 5.8 | 5556 | 5.2 | 9.1 | 29.4 | 138.9 | 24737 | | 483.9 |
| 906.43 | 13 | aA(14)AAAAITLKVa-NH2 | 760.57 SAAS | 0.50 | 46.67 | 1.9 | 1360 | 1.7 | 15.6 | 9.5 | 49.0 | 392 | 1875.0 | 24.7 |
| 906.44 | 13 | aA(14)AAAAITLKFa-NH2 | 760.57 SAAS | 1.70 | 3033.33 | 2.0 | 261 | 3.8 | 33.3 | 103.6 | 25.0 | 81 | 821.0 | 168.7 |
| 906.45 | 13 | aA(14)AAAAITLKIa-NN2 | 760.57 SAAS | 1.00 | | 2.5 | 4455 | 2.0 | 19.2 | 28.2 | 25.0 | 84 | | 56.2 |
| 906.46 | 13 | aA(14)AAAAITLKAKa-NH2 | 760.57 SAAS | | | | | | | | | | | |
| 906.47 | 13 | aA(14)AAAAITLKAEa-NH2 | 760.57 SAAS | 1.50 | | 5.2 | 30000 | 2.7 | 8.2 | 25.5 | 131.6 | 3917 | | 60.2 |
| 906.48 | 13 | aA(14)AAAAITLKAQa-NH2 | 760.57 SAAS | 0.70 | | 2.1 | 12152 | 2.3 | 5.5 | 20.0 | 96.2 | 2938 | | 18.4 |
| 906.49 | 13 | aA(14)AAAAITLKAVa-NH2 | 760.57 SAAS | 0.60 | | 2.1 | 24446 | 3.2 | 3.4 | 4.5 | 28.4 | 4273 | | 14.6 |
| 906.50 | 13 | aA(14)AAAAITLKAFa-NH2 | 760.57 SAAS | 0.30 | 15.59 | 3.7 | 584 | 1.7 | 3.2 | 9.5 | 73.5 | 2238 | 25.9 | 20.0 |

TABLE IX

PADRE Class II Binding Affinities

| PEPTIDE | LEN | SEQUENCE | SOURCE | DR1 nM | DR2w261 nM | DR2w282 nM | DR3 nM | DR4w4 nM | DR4w14 nM | DR5 nM | DR7 nM | DR52a nM | DRw53 nM | DOG.1 nM |
|---|---|---|---|---|---|---|---|---|---|---|---|---|---|---|
| 965.011 | 13 | aK(14)VKANTLKAAa-NH2 | Pan DR epitopes | 1.50 | | 12.5 | 592 | 2.8 | 3.6 | 11.8 | 480.8 | | | |
| 965.012 | 13 | aK(14)VKANTLKAAa-NH2 | Pan DR epitopes | 1.30 | | 10.5 | 4592 | 2.1 | 5.9 | 2.2 | 781.3 | | | |
| 965.021 | 13 | aK(14)VKAAWTLKAAa-NH2 | Pan DR epitopes | 0.80 | | 5.7 | 1098 | 1.5 | 4.5 | 4.1 | 89.3 | | | |
| 965.022 | 13 | aK(14)VKAWTLKAAa-NH2 | Pan DR epitopes | 0.70 | | 9.0 | 12162 | 0.8 | 1.5 | 1.1 | 337.8 | | | |
| 965.031 | 13 | aK(14)VWANTLKAAa-NH2 | Pan DR epitopes | 0.80 | | 5.4 | 346 | 2.1 | 5.2 | 8.3 | 208.3 | | | |
| 965.032 | 13 | aK(14)VWANTLKAAa-NH2 | Pan DR epitopes | 0.50 | 233.33 | 9.0 | 849 | 0.7 | 2.9 | 2.9 | 347.2 | 17407 | 260.9 | 1666.7 |
| 965.041 | 13 | aK(14)VWAYTLKAAa-NH2 | Pan DR epitopes | 0.50 | | 2.5 | 136 | 0.5 | 2.6 | 4.7 | 156.3 | | | |
| 965.042 | 13 | aK(14)VWAYTLKAAa-NH2 | Pan DR epitopes | 0.20 | | 9.5 | 3462 | 1.0 | 3.3 | 3.9 | 657.9 | | | |
| 965.051 | 13 | aK(14)VYAAWTLKAAa-NH2 | Pan DR epitopes | 0.50 | | 7.1 | 281 | 0.3 | 4.2 | 5.7 | 833.3 | | | |
| 965.052 | 13 | aK(14)VYAWTLKAAa-NH2 | Pan DR epitopes | 0.70 | | 9.0 | 16071 | 0.8 | 5.5 | 6.9 | 25.5 | | | |
| 965.06 | 13 | aR(14)VRANTLKAAa-NH2 | Pan DR epitopes | 0.80 | | 6.4 | 8333 | 1.3 | 5.0 | 5.6 | 73.5 | | | |
| 965.071 | 13 | aK(14)VKAHTLKAAa-NH2 | Pan DR epitopes | 1.60 | | 5.1 | 4945 | 1.8 | 9.4 | 10.5 | 166.7 | | | |
| 965.072 | 13 | aK(14)VKAHTLKAAa-NH2 | Pan DR epitopes | 1.20 | | 6.6 | 6429 | 1.4 | 5.7 | 4.8 | 555.6 | | 103.4 | |
| 965.081 | 13 | aK(14)VAANTLKAAa-NH2 | Pan DR epitopes | 1.20 | | 3.7 | 450 | 3.0 | 17.2 | 8.0 | 192.3 | | | |
| 965.082 | 13 | aK(14)VAANTLKAAa-NH2 | Pan DR epitopes | 0.70 | | 7.1 | 3214 | 1.3 | 5.0 | 12.5 | 113.6 | | | |
| 965.091 | 13 | aK(14)VAAYTLKAAa-NH2 | Pan DR epitopes | 0.80 | | 7.4 | 450 | 1.0 | 8.8 | 5.4 | 192.3 | | 54.5 | |
| 965.092 | 13 | aK(14)VAAYTLKAAa-NH2 | Pan DR epitopes | 0.60 | | 6.4 | 3214 | 1.0 | 6.6 | 6.5 | 54.3 | | | |
| 965.10 | 13 | aK(14)VAAWTLKAAa-NH2 | Pan DR epitopes | 1.20 | 39.57 | 5.5 | 214 | 2.8 | 12.2 | 11.1 | 147.1 | 979 | 89.6 | 25.0 |
| 965.14 | 13 | aKi14)VAAKTLKAAa-NH2 | Pan DR epitopes | 3.60 | | 8.0 | 1406 | 7.4 | 78.1 | 34.5 | 227.3 | | 33.3 | |
| 955.15 | 13 | aK(14)VAAHTLKAAa-NH2 | Pan DR epitopes | 1.90 | | 5.4 | 2500 | 3.2 | 17.2 | 29.9 | 156.3 | | 50.0 | |
| 965.16 | 13 | aK(14)VAAATLKAAa-NH2 | Pan DR epitopes | 4.20 | | 6.0 | 2647 | 6.2 | 69.4 | 16.7 | 227.3 | | 83.3 | |
| 965.17 | 13 | AK(14)VAAWTLKAAA-NH2 | Pan DR epitopes | 2.00 | | 5.8 | 3214 | 3.8 | 33.3 | 9.1 | 147.1 | | 107.1 | |
| 965.19 | 16 | KSSaK(14)VMAATLKAAA-NH2 | Pan DR epitopes | 10.20 | | 23.5 | | 5.5 | 41.7 | 9.1 | 378.8 | | | |

Note:
(14) = cyclohexylalanine;
AK(14)VAAWTLKAAAA-NH2= SEQ ID NO:21.

f. Conclusion

Peptide analogs with broader specificity and higher affinity than known DR binding peptides may be generated by introducing various substitutions at non-critical motif residues, followed by combining these favorable substitutions into next generation peptide analogs.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. A composition for eliciting an immune response to an immunogen, the composition comprising a pan DR binding oligopeptide of less than about 50 residues and the immunogen, the pan DR binding oligopeptide comprising a peptide of the formula $R_1$-$R_2$-$R_3$-$R_4$-$R_5$, wherein:

$R_1$ is a D- or an L-amino acid followed by lysine;

$R_2$ is selected from the group consisting of cyclohexylalanine, tyrosine, or phenylalanine;

$R_3$ is 3 or 4 amino acids, wherein each amino acid is independently selected from the group consisting of alanine, isoleucine, serine and valine;

$R_4$ is selected from the group consisting of threonine-leucine-lysine, lysine-threonine, or tryptophan-threonine-leucine-lysine; and $R_5$ consists of 2 to 4 amino acids followed by a D- or an L-amino acid wherein each of the 2 to 4 amino acids is independently selected from the group consisting of alanine, serine, and valine.

2. The composition of claim 1, wherein $R_4$ is tryptophan-threonine-leucine-lysine.

3. The composition of claim 1, wherein the immunogen is an antibody-inducing determinant.

4. The composition of claim 1, wherein the immunogen is a lipid.

5. The composition of claim 3, wherein the pan DR binding oligopeptide and the antibody inducing determinant are admixed.

6. The composition of claim 3, wherein the pan DR binding oligopeptide and the antibody inducing determinant are linked.

7. The composition of claim 1, wherein the immunogen is a peptide.

8. The composition of claim 7, wherein the peptide is a CTL inducing-peptide.

9. The composition of claim 7, wherein the peptide is an antibody-inducing peptide.

10. The composition of claim 7, wherein the pan DR binding oligopeptide and the peptide are linked.

11. The composition of claim 10, wherein the peptide is a T-helper epitope.

12. The composition of claim 7, wherein the peptide is linked to the pan DR binding oligopeptide through a linker.

13. The composition of claim 12, wherein the linker comprises an alanine residue.

14. The composition of claim 12, wherein the linker comprises an amino acid mimetic.

15. The composition of claim 7, wherein the peptide is linked to the C-terminus of the pan DR binding oligopeptide.

16. The composition of claim 7, wherein the peptide is linked to the N-terminus of the pan DR binding oligopeptide.

17. The composition of claim 1, wherein the immunogen is derived from a virus.

18. The composition of claim 1, wherein the immunogen is derived from a cancer cell.

19. The composition of claim 1, wherein the pan DR binding oligopeptide is covalently linked to a lipid moiety.

20. The composition of claim 1, wherein the pan DR binding oligopeptide is AKXVAAWTLKAAA (SEQ ID NO:27) or AKFVAAWTLKAAA (SEQ ID NO:28).

21. A pharmaceutical composition comprising a pharmaceutically acceptable carrier, an immunogen and a pan DR binding oligopeptide of less than about 50 residues,
the pan DR binding oligopeptide comprising a peptide of the formula is $R_1$-$R_2$-$R_3$-$R_4$-$R_5$, wherein:
$R_1$ is a D- or an L-amino acid followed by lysine;
$R_2$ is selected from the group consisting of cyclohexylalanine, tyrosine, or phenylalanine;
$R_3$ is 3 or 4 amino acids, wherein each amino acid is independently selected from the group consisting of alanine, isoleucine, serine and valine;
$R_4$ is selected from the group consisting of threonine-leucine-lysine, lysine-threonine, or tryptophan-threonine-leucine-lysine; and
$R_5$ consists of 2 to 4 amino acids followed by a D- or an L-amino acid wherein each of the 2 to 4 amino acids is independently selected from the group consisting of alanine, serine, and valine.

22. The composition of claim 21, further comprising an adjuvant.

23. The composition of claim 21, wherein the adjuvant is selected from the group consisting of Freund's complete adjuvant or Freund's incomplete adjuvant, alum, aluminum phosphate and aluminum hydroxide.

24. A method of inducing a humoral immune response comprising introduction into a mammal the composition of claim 21.

25. The method of claim 24, wherein the introduction is parenteral.

26. The method of claim 24, wherein the immune response is prophylactic.

27. The method of claim 24, wherein the immune response is therapeutic.

28. A composition for eliciting an immune response to an immunogen, the composition comprising a pan DR binding oligopeptide of less than about 50 residues and the immunogen,
the pan DR binding oligopeptide comprising a peptide of the formula $R_1$-$R_2$-$R_3$-$R_4$-$R_5$, wherein:
$R_1$ is a D- or an L-amino acid followed by alanine or lysine;
$R_2$ is selected from the group consisting of cyclohexylalanine, tyrosine, or phenylalanine;
$R_3$ is 3 or 4 amino acids, wherein each amino acid is independently selected from the group consisting of alanine, isoleucine, serine and valine;
$R_4$ is selected from the group consisting of threonine-leucine-lysine, lysine-threonine, or tryptophan-threonine-leucine-lysine; and
$R_5$ consists of 2 to 4 amino acids followed by a D- or an L-amino acid wherein each of the 2 to 4 amino acids is independently selected from the group consisting of serine and valine.

29. The composition of claim 28, wherein the immunogen is an antibody-inducing determinant.

30. The composition of claim 28, wherein the immunogen is a lipid.

31. The composition of claim 29, wherein the pan DR binding oligopeptide and the antibody-inducing determinant are admixed.

32. The composition of claim 29, wherein the pan DR binding oligopeptide and the antibody inducing determinant are linked.

33. The composition of claim 28, wherein the immunogen is a peptide.

34. The composition of claim 33, wherein the peptide is a CTL-inducing peptide.

35. The composition of claim 33, wherein the peptide is an antibody-inducing peptide.

36. The composition of claim 33, wherein the pan DR binding oligopeptide and the peptide are linked.

37. The composition of claim 36, wherein the peptide is a T-helper epitope.

38. The composition of claim 33, wherein the peptide is linked to the pan DR binding oligopeptide through a linker.

39. The composition of claim 38, wherein the linker comprises an alanine residue.

40. The composition of claim 38, wherein the linker comprises an amino acid mimetic.

41. The composition of claim 33, wherein the peptide is linked to the C-terminus of the pan DR binding oligopeptide.

42. The composition of claim 33, wherein the peptide is linked to the N-terminus of the pan DR binding oligopeptide.

43. The composition of claim 28, wherein the immunogen is derived from a virus.

44. The composition of claim 28, wherein the immunogen is derived from a cancer cell.

45. The composition of claim 28, wherein the pan DR binding oligopeptide is covalently linked to a lipid moiety.

46. A pharmaceutical composition comprising a pharmaceutically acceptable carrier, an immunogen and a pan DR binding oligopeptide of less than about 50 residues,
the pan DR binding oligopeptide comprising a peptide of the formula $R_1$-$R_2$-$R_3$-$R_4$-$R_5$, wherein:
$R_1$ is a D- or an L-amino acid followed by alanine or lysine;
$R_2$ is selected from the group consisting of cyclohexylalanine, tyrosine, or phenylalanine;
$R_3$ is 3 or 4 amino acids, wherein each amino acid is independently selected from the group consisting of alanine, isoleucine, serine and valine;
$R_4$ is selected from the group consisting of threonine-leucine-lysine, lysine-threonine, or tryptophan-threonine-leucine-lysine; and
$R_5$ consists of 2 to 4 amino acids followed by a D- or an L-amino acid wherein each of the 2 to 4 amino acids is independently selected from the group consisting of serine and valine.

47. The composition of claim 46, further comprising an adjuvant.

48. The composition of claim 47, wherein the adjuvant is selected from the group consisting of Freund's complete adjuvant or Freund's incomplete adjuvant, alum, aluminum phosphate and aluminum hydroxide.

49. A method of inducing a humoral immune response comprising introduction into a mammal the composition of claim 46.

50. The method of claim 49, wherein the introduction is parenteral.

51. The method of claim 49, wherein the immune response is prophylactic.

52. The method of claim 49, wherein the immune response is therapeutic.

* * * * *

UNITED STATES PATENT AND TRADEMARK OFFICE
CERTIFICATE OF CORRECTION

PATENT NO. : 6,413,935 B1
DATED : July 2, 2002
INVENTOR(S) : Sette et al.

It is certified that error appears in the above-identified patent and that said Letters Patent is hereby corrected as shown below:

<u>Title page,</u>
Item [75], Inventors, please delete the name "Jeffrey" and insert -- Jeffery --.

Signed and Sealed this

Seventeenth Day of December, 2002

JAMES E. ROGAN
*Director of the United States Patent and Trademark Office*